(12) United States Patent
Patel et al.

(10) Patent No.: US 11,328,815 B2
(45) Date of Patent: *May 10, 2022

(54) PHYSICAL MEASUREMENT OF EMPIRICAL INDICATORS OF PATIENT-RELATED OUTCOME VALUE USING TIME AND MOTION SENSOR RESULTS

(71) Applicant: MEDPATHER, INC., Austin, TX (US)

(72) Inventors: Mrigasha Patel, Minneapolis, MN (US); Ryan Egeland, Wayzata, MN (US); Brent Egeland, Austin, TX (US)

(73) Assignee: MEDPATHER, INC., Austin, TX (US)

( * ) Notice: Subject to any disclaimer, the term of this patent is extended or adjusted under 35 U.S.C. 154(b) by 235 days.

This patent is subject to a terminal disclaimer.

(21) Appl. No.: 16/450,733

(22) Filed: Jun. 24, 2019

(65) Prior Publication Data
US 2019/0311800 A1 Oct. 10, 2019

Related U.S. Application Data

(60) Continuation-in-part of application No. 15/982,992, filed on May 17, 2018, now Pat. No. 10,332,627,
(Continued)

(51) Int. Cl.
*G16H 40/20* (2018.01)
*H04L 43/10* (2022.01)
(Continued)

(52) U.S. Cl.
CPC ............... *G16H 40/20* (2018.01); *G06N 5/02* (2013.01); *G16H 10/60* (2018.01); *G16H 40/40* (2018.01);
(Continued)

(58) Field of Classification Search
CPC ... G06F 17/60; G16H 40/20; G06Q 50/22–24
See application file for complete search history.

(56) References Cited

U.S. PATENT DOCUMENTS 10,102,926 B1 * 10/2018 Leonardi ................ G16H 50/20
2002/0165733 A1 * 11/2002 Pulkkinen .............. G16H 40/67
705/2

(Continued)

OTHER PUBLICATIONS

"Using Tracking Tools to Improve patient Flow in Hospitals"; California Healthcare Foundation; Dec. 2017 (Year: 2017).*
(Continued)

*Primary Examiner* — John A Pauls
(74) *Attorney, Agent, or Firm* — Dickinson Wright PLLC

(57) ABSTRACT

A system, a method and non-transitory computer readable medium are provided. The method includes receiving a message from a gateway. The message includes an identification parameter associated with the gateway that received a ping from a beacon. The message also includes a beacon identifier of the beacon that transmitted the ping, the ping included the beacon identifier. The message further includes a derived signal strength parameter that indicates a proximity of the beacon to the gateway when the beacon transmitted the ping. The method also includes acquiring an outcome associated with medical-care that is provided by a medical provider to a patient. The method further includes identifying a cost associated with the medical-care provided by the medical provider based in part on the received message. The method additionally includes generating a value score that relates the identified cost of providing the medical-care to the patient, to the acquired outcome.

19 Claims, 8 Drawing Sheets

Related U.S. Application Data which is a division of application No. 15/885,621, filed on Jan. 31, 2018, now Pat. No. 10,056,159.

(51) Int. Cl.
*G16H 40/40* (2018.01)
*H04L 12/66* (2006.01)
*G06N 5/02* (2006.01)
*G16H 10/60* (2018.01)
*H04W 64/00* (2009.01)

(52) U.S. Cl.
CPC ............ *H04L 12/66* (2013.01); *H04L 43/10* (2013.01); *H04W 64/00* (2013.01)

(56) References Cited

U.S. PATENT DOCUMENTS

| | | | |
|---|---|---|---|
| 2003/0078911 A1* | 4/2003 | Haskell | G16H 40/20 |
| 2009/0048865 A1* | 2/2009 | Breazeale, Jr. | G06Q 10/00 |
| | | | 705/2 |
| 2010/0274588 A1 | 10/2010 | Choubey | |
| 2012/0078651 A1 | 3/2012 | Henderson et al. | |
| 2012/0264447 A1 | 10/2012 | Rieger | |
| 2015/0019241 A1* | 1/2015 | Bennett | G16H 50/20 |
| | | | 705/2 |
| 2015/0310180 A1* | 10/2015 | Pattekar | G16H 40/20 |
| | | | 705/2 |
| 2016/0098805 A1 | 4/2016 | Vavroch et al. | |
| 2016/0140304 A1* | 5/2016 | Myers, Jr. | G06F 3/0482 |
| | | | 705/2 |
| 2016/0371444 A1* | 12/2016 | Fidone | G16H 10/60 |

OTHER PUBLICATIONS

"Survey of Wireless Indoor Positioning Techniques and Systems", Liu, et al.; IEEE Transaction on Systems, Man and Cybernetics, vol. 37, No. 6; Nov. 6, 2007.

* cited by examiner

PHYSICAL MEASUREMENT OF EMPIRICAL INDICATORS OF PATIENT-RELATED OUTCOME VALUE USING TIME AND MOTION SENSOR RESULTS

CROSS-REFERENCE TO RELATED APPLICATION AND CLAIM OF PRIORITY

This patent application is a continuation-in-part of and claims priority to U.S. patent application Ser. No. 15/982,992 filed on May 17, 2018 (now U.S. Pat. No. 10,332,627), which is a division of and claims priority to U.S. patent application Ser. No. 15/885,621 filed on Jan. 31, 2018 (now U.S. Pat. No. 10,056,159). The above-identified patent applications are both hereby incorporated by reference in their entirety.

TECHNICAL FIELD

This disclosure relates generally to management of medical resources. More specifically, this disclosure relates deriving a value for value based healthcare resulting from time based expenditure and physical measurement of empirical indicators of patient-related outcome.

BACKGROUND

Each year, tens of millions of individuals seek or need the assistance of healthcare professionals and medical facilities. As such, healthcare is one of the largest industries in the country. However, the cost of healthcare is rising at an ever-increasing rate. Controlling and managing the rising cost of healthcare while providing quality medical-care is a difficult equilibrium. Medical providers and facilities often struggle to provide quality care when the medical providers and facilities are not getting paid due to the increase in healthcare and medical expenses. As such, medical providers and medical facilities often struggle to predict the best allocation of resources as well as forecasting revenue, in order to provide quality care.

An ability to eliminate or reduce wasteful procedures while lowering overpriced services are often suggested to help reduce healthcare and medical expenses. Various models of healthcare cost prediction are typically not accurate. For example, one methods of predicting medical costs is based on an economic model using standard demographic data (such as age and sex), but does not take actual real time data. Predictive modeling of medical resources based on actual use is not as helpful due to the numerous parts of in a hospital setting.

SUMMARY

This disclosure provides system and method for physical measurement of empirical indicators of patient-related outcome value using time and motion sensor results. In one embodiment, a system for value derivation is provided. The system includes one or more gateways and a computing device. The one or more gateways are located in predefined locations within a medical facility. Each of the one or more gateways includes a transceiver, a first processor, and an identification parameter. The identification parameter is unique to each of the one or more gateways and corresponds to each of the predefined locations. The transceiver is configured to receive a ping from a beacon, the ping includes a beacon identifier that is unique to the beacon, wherein the beacon is associated with a medical provider or a patient. The transceiver is also configured to transmit a message to the computing device in response to receiving the ping. The first processor is operably connected to the transceiver. The first processor is configured to derive a signal strength parameter associated with the received ping, the signal strength parameter indicates strength of the received ping. The first processor is also configured to generate the message that includes the beacon identifier, the identification parameter associated with one gateway that received the ping, and the signal strength parameter. The computing device of the system includes a communication interface and a second processor. The communication interface is operably connected to the second processor and configured to receive the message. The second processor is configured to acquire an outcome associated with medical-care that is provided by the medical provider to the patient. The second processor is also configured to identify a cost associated with the medical-care provided by the medical provider to the patient based on the received message. The second processor is further configured to generate a value score that relates the identified cost of the medical-care provided by the medical provider to the patient, to the acquired outcome In another embodiment a method is provided. The method includes receiving a message from a gateway. The message includes an identification parameter associated with the gateway that received a ping from a beacon. The message also includes a beacon identifier of the beacon that transmitted the ping to the gateway, the ping included the beacon identifier. The message further includes a derived signal strength parameter, the derived signal strength parameter indicates a proximity of the beacon to the gateway when the beacon transmitted the ping. The method also includes acquiring an outcome associated with medical-care that is provided by a medical provider to a patient. The method further includes identifying a cost associated with the medical-care provided by the medical provider to the patient based in part on the received message from the gateway. The method additionally includes generating a value score that relates the identified cost of providing the medical-care by the medical provider to the patient, to the acquired outcome.

In yet another embodiment a non-transitory computer readable medium embodying a computer program is provided. The computer program comprising program code that when executed causes at least one processor to: receive a message from a gateway, the message includes: an identification parameter associated with the gateway that received a ping from a beacon, a beacon identifier of the beacon that transmitted the ping to the gateway, the ping included the beacon identifier, and a derived signal strength parameter, the derived signal strength parameter indicates a proximity of the beacon to the gateway when the beacon transmitted the ping; acquire an outcome associated with medical-care that is provided by a medical provider to a patient; identify a cost associated with the medical-care provided by the medical provider to the patient based in part on the received message from the gateway; and generate a value score that relates the identified cost of providing the medical-care by the medical provider to the patient, to the acquired outcome.

Other technical features may be readily apparent to one skilled in the art from the following figures, descriptions, and claims.

Before undertaking the DETAILED DESCRIPTION below, it may be advantageous to set forth definitions of certain words and phrases used throughout this patent document. The term "couple" and its derivatives refer to any direct or indirect communication between two or more elements, whether or not those elements are in physical contact with one another. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrase "associated with," as well as derivatives thereof, means to include, be included within, interconnect with, contain, be contained within, connect to or with, couple to or with, be communicable with, cooperate with, interleave, juxtapose, be proximate to, be bound to or with, have, have a property of, have a relationship to or with, or the like. The term "controller" means any device, system or part thereof that controls at least one operation. Such a controller may be implemented in hardware or a combination of hardware and software and/or firmware. The functionality associated with any particular controller may be centralized or distributed, whether locally or remotely. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for other certain words and phrases are provided throughout this patent document. Those of ordinary skill in the art should understand that in many if not most instances, such definitions apply to prior as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

Figure 1:
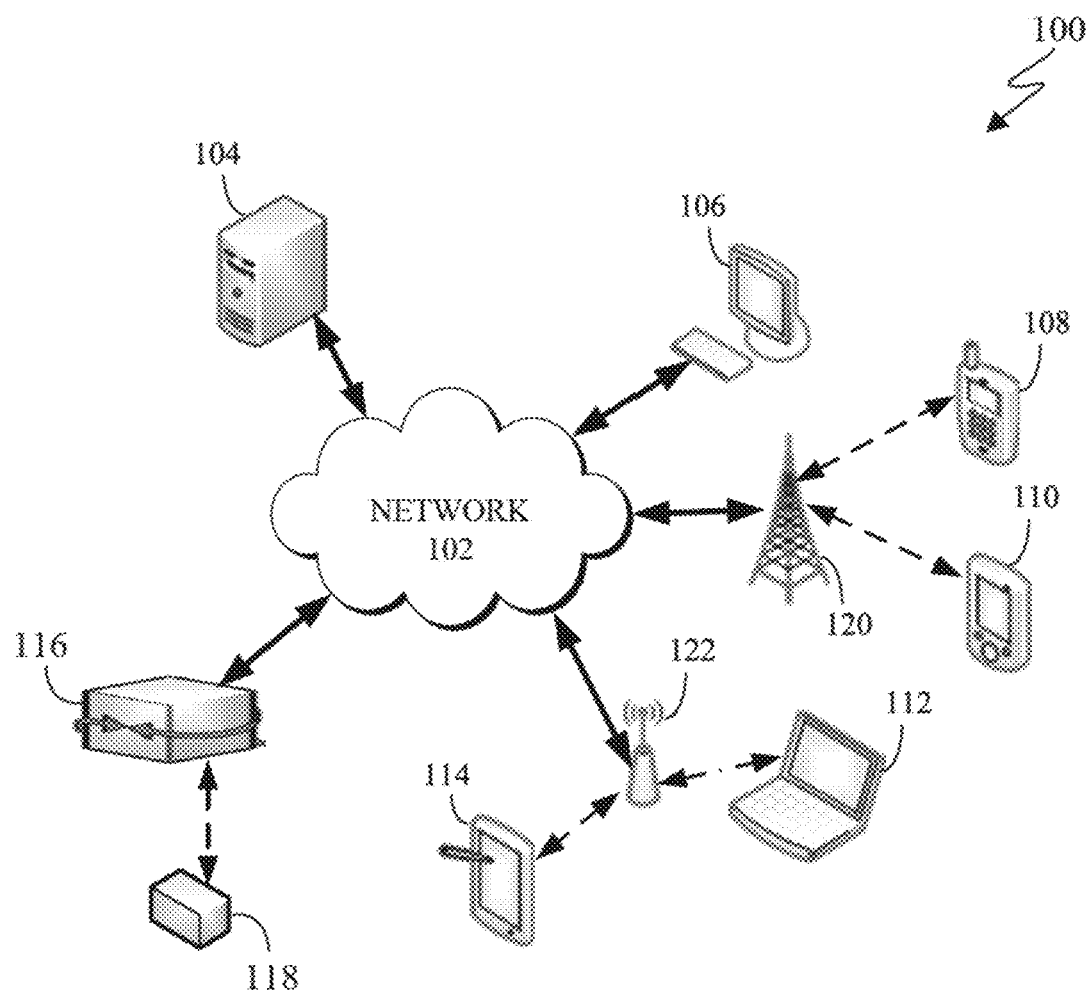
FIG. 1 illustrates an example communication system in accordance with embodiments of the present disclosure.

FIGS. 1 through 8, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably-arranged wireless communication system or device.

According to embodiments of the present disclosure, various methods for tracking individuals (such as patients and medical providers) and equipment are provided. In certain embodiments, beacons are carried by patients, medical providers, staff, and are affixed to equipment. In certain embodiments, gateways are located throughout the medical facility to receive pings from the beacons. For example, a gateway can be located in various rooms where patients typically are located, such as a waiting room, an exam room, a medical imaging room, a diagnostic testing room, an operating room, and the like.

Fee for service medical-care is a system of providing medical-care where providers such as doctors, physician assistants, nurse practitioners, therapist (including speech therapists, physical therapists, occupational therapists, and the like), nurses, and the like, are paid for each individual medical service rendered to a patient. For example, every office visit, test, examination, procedure performed has a price tag associated therewith. By associating a fee for each office visit, and procedure performed incentivizes medical providers to provide more treatments and services. For example, fee for service medical-care can cause an increase in the quantity of tests and procedures rather than quality of services provided to a patient. For instance, a provider can order a number of tests and procedures for a patient while the patient outcomes may not necessarily improve in proportion to the monetary expenditures of each additional test.

Value based healthcare is a system that focuses on quality of medical-care provided to a patient. In particular, value based healthcare maximizes value for patients based on outcomes received and costs or expenditures to achieve that outcome. For example, value based healthcare attempts to relate the quality of patient care to the costs of rendering such care by focusing on the patients outcomes for services rendered.

According to embodiments of the present disclosure determining a value for a patient poses significant challenges as both outcomes and costs can fluctuate significantly. For example, identifying outcomes for of medical-care and intervention can vary drastically. Similarly, identified costs can vary from one medical facility to another for the same or similar medical-care. Additionally, with respect to medical insurance, a medical facility can send two insurance companies identical bills for the same procedure performed on separate individuals. Each insurance company can then pay a fraction of the bill based on the contracted rate with the medical facility. It is noted that the insurance companies may not necessarily pay the same amount, resulting in different costs associated with the same procedure.

Embodiments of the present disclosure recognize and take into consideration the various differences between outcomes and costs can be associated with value based healthcare. In certain embodiments, a standardized foundation for equating outcomes to dollars spent is disclosed in order to identify a value that a patient receives for medical-care. For example, outcomes can be relating measured results, questionnaires, demographic information, in relation to the specific condition being treated by the medical provider. In another example, costs can be derived by accumulating the costs each patient accrues during a visit to the medical facility coupled with costs associated with the various tests and procedures administered to the patient. According to embodiments of the present disclosure, various methods for deriving a cost associated with a particular location within a medical facility are provided. In certain embodiments, various rooms can have different costs associated with each room. For example, the cost associated with a waiting room is less than an exam room, while the cost associated with an exam room is less than a medical imaging room. The cost for a waiting room can be allocated based on the size of the room and the rent associated with the size as well as the value of the furniture in the room. The cost associated with an exam room can be allocated by the size of the room and the rent associated therewith as well as the cost of the equipment located in the room. In certain embodiments, the costs can also include the salary of the medical provider.

Embodiments of the present disclosure provide for situations in which an electronic device, such as mobile device, can function as a beacon for a location to a gateway. For example, a person typically carries a mobile device, such as a smart phone, with them constantly. When the mobile device is in proximity to a gateway, the gateway can transmit a message to a server. The message indicates that a mobile device associated with a particular individual is within proximity to the gateway. The server can then derive the location of the mobile device and the individual to whom carries the mobile device. In certain embodiments, the gateway can also transmit a message when the beacon, such as a mobile device, is no longer in proximity to the gateway. This allows the server to derive a duration of time that the person was in a specific location. By deriving the time data associated with a patient and the interaction time between the patient and a medical provider can establish a standardized price schema to derive a value. Further, by deriving locations of a patient throughout a medical facility can also establish particular outcomes. For example, if the patient goes from the operating room to the morgue, the outcome was death. In another example, if the patient goes from the Intensive Care Unit (ICU) to exiting the medical facility, derived positive outcome can be established for the patient.

FIG. 1 illustrates an example system 100 according to this disclosure. The embodiment of the system 100 shown in FIG. 1 is for illustration only. Other embodiments of the system 100 could be used without departing from the scope of this disclosure.

The system 100 includes network 102 that facilitates communication between various components in the system 100. For example, the network 102 can communicate Internet Protocol (IP) packets, frame relay frames, Asynchronous Transfer Mode (ATM) cells, or other information between network addresses. The network 102 includes one or more local area networks (LANs), metropolitan area networks (MANs), wide area networks (WANs), all or a portion of a global network such as the Internet, or any other communication system or systems at one or more locations.

The network 102 facilitates communications between various server(s) 104 and various client devices 106-118. The client devices 106-118 may be, for example, a mobile device, a smart phone, a personal digital assistant (PDA) a tablet computer, a laptop, a personal computer, a wearable device; a tracking device (such as a beacon), a gateway device or a combination thereof.

The server 104 can represent one or more servers. Each server 104 includes any suitable computing or processing device that can provide computing services for one or more client devices. Each server 104 could, for example, include one or more processing devices, one or more memories storing instructions and data, and one or more network interfaces facilitating communication over the network 102. As described in more detail below with respect to FIG. 2, the server 104 derives values by receiving locations of beacons associated with persons and equipment, and outcomes associated with patients that are provided medical-care by a medical provider.

Each client device 106-118 represents any suitable computing or processing device that interacts with at least one server or other computing device(s) over the network 102. In this example, the client devices 106-118 include a desktop computer 106, a mobile telephone or mobile devices 108 (such as a smartphone), a PDA 110, a laptop computer 112, a tablet computer 114, a gateway 116, and a beacon 118. However, any other or additional client devices could be used in the system 100.

In this example, some of the client devices 108-114 and 118 communicate indirectly with the network 102. For example, the client devices 108 and 110 (the mobile devices and the PDA, respectively) communicate via one or more base stations 120, such as cellular base stations or eNodeBs (eNBs). Also, the client devices 112 and 114 (the laptop computer and the tablet computer, respectively) communicate via one or more wireless access points 122, such as IEEE 802.11 wireless access points. In certain embodiments, the gateway 116 communicates directly with the network 102. In certain embodiments, the gateway 116 communicates with the network 102 via the wireless access point 122. The beacon 118 communicates with the network 102 through the gateway 116. In certain embodiments, the beacon 118 communicates with the gateway 116 through a short range frequency communication channel such as BLUETOOTH, BLUETOOTH LOW ENERGY (BLE), WI-FI, radio frequency identification (RFID), or the like. Note that these are for illustration only and that each client device 106-118 could communicate directly with the network 102 or indirectly with the network 102 via any suitable intermediate device(s) or network(s).

In certain embodiments, the mobile device 108 (or any other client device 106-118) can transmit information securely and efficiently to another device, such as, for example, the server 104. The gateway 116 (or any other client device 106-114 and 118) can trigger the information transmission between itself and the server 104. In certain embodiments, the mobile device 108, the laptop computer 112, or the tablet computer 114 can function as the beacon 118. In certain embodiments, the mobile device 108, the laptop computer 112, or the tablet computer 114 can function as the gateway 116.

Although FIG. 1 illustrates one example of a system 100, various changes can be made to FIG. 1. For example, the system 100 could include any number of each component in any suitable arrangement. In general, computing and communication systems come in a wide variety of configurations, and FIG. 1 does not limit the scope of this disclosure to any particular configuration. While FIG. 1 illustrates one operational environment in which various features disclosed in this patent document can be used, these features could be used in any other suitable system.

The processes and systems provided in this disclosure allow for the beacon 118, or the gateway 116, to provide location information of an individual or equipment within a medical facility. In certain embodiments, the beacon 118 is affixed to an individual or a piece of equipment. The gateway 116 receives a ping (such as a signal message) from the beacon and transmits a generated message to the server 104. The server 104 can then ascertain a location of the beacon and as a result the individual or equipment associated with the beacon.

Figure 2:
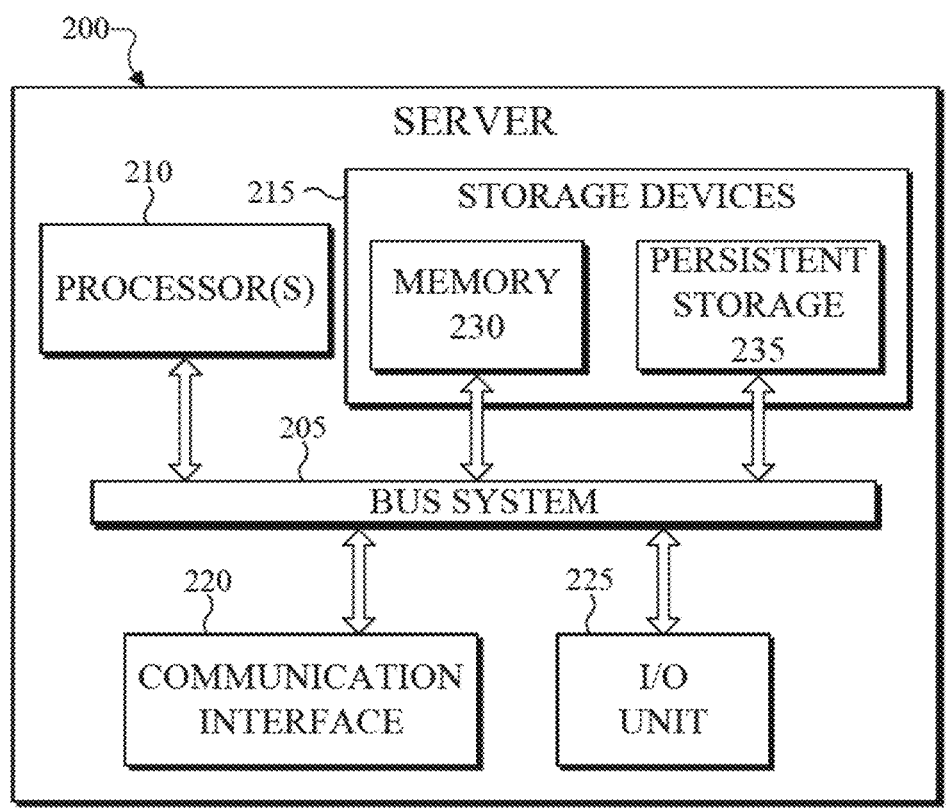
FIG. 2 illustrates an example server device in accordance with embodiments of the present disclosure.
Figure 3:
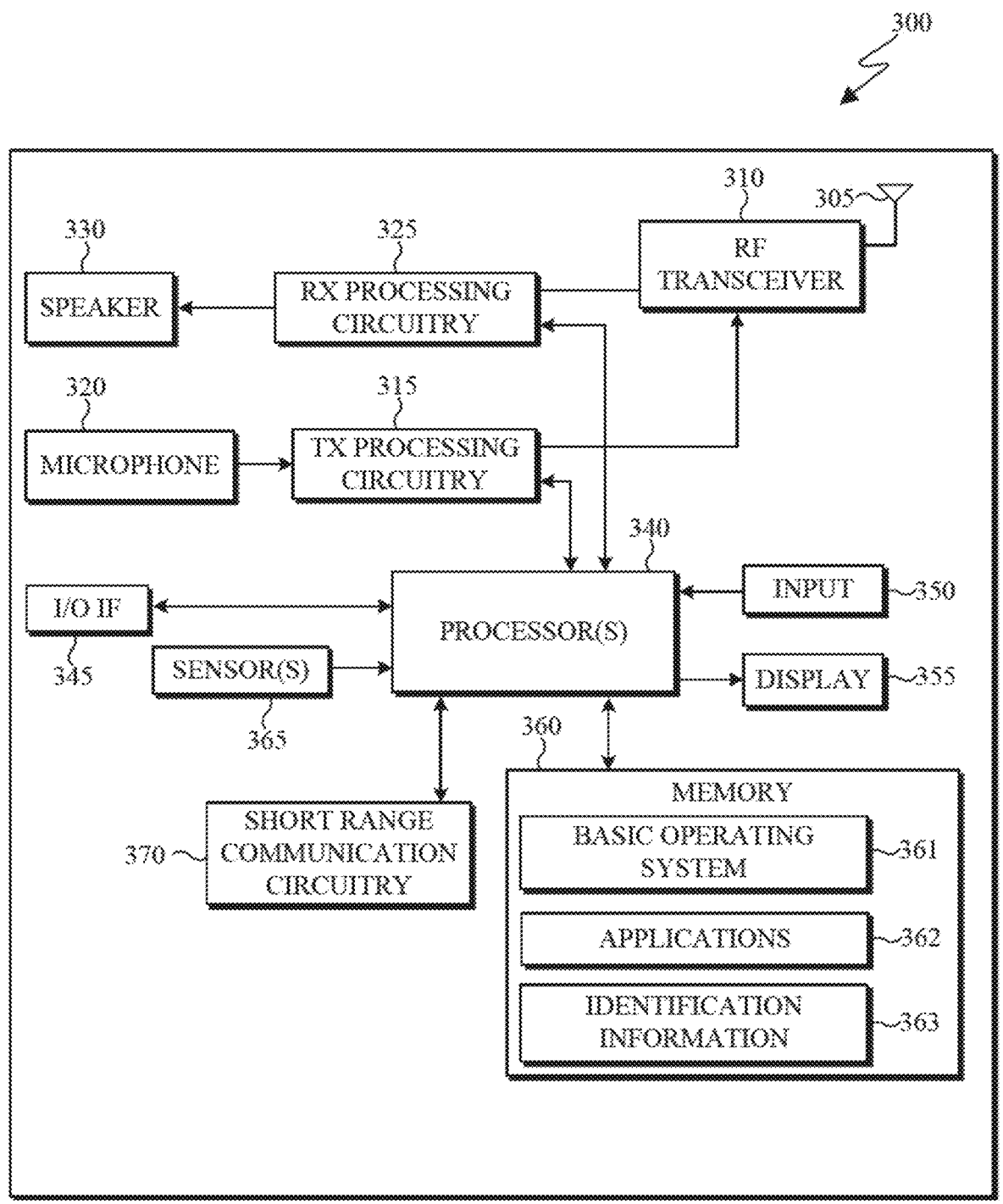
FIG. 3 illustrates an example block diagram in accordance with embodiments of the present disclosure.

FIGS. 2 and 3 illustrate example devices in a computing system in accordance with an embodiment of this disclosure. In particular, FIG. 2 illustrates an example server 200, and FIG. 3 illustrates an example electronic device 300. The server 200 could represent the server 104 in FIG. 1, and the electronic device 300 could represent one or more of the client devices 106-118 in FIG. 1.

Server 200 can represent one or more local servers, one or more location servers, or one or more predictive cost analysis server, or a value derivation server. As shown in FIG. 2, the server 200 includes a bus system 205 that supports communication between at least one processor(s) 210, at least one storage device(s) 215, at least one communication interface 220, and at least one input/output (I/O) unit 225.

The processor 210 executes instructions that can be stored in a memory 230. The processor 210 can include any suitable number(s) and type(s) of processors or other devices in any suitable arrangement. Example types of processor(s) 210 include microprocessors, microcontrollers, digital signal processors, application specific integrated circuits, and discreet circuitry.

The memory 230 and a persistent storage 235 are examples of storage devices 215 that represent any structure(s) capable of storing and facilitating retrieval of information (such as data, program code, or other suitable information on a temporary or permanent basis). The memory 230 can represent a random access memory or any other suitable volatile or non-volatile storage device(s). The persistent storage 235 can contain one or more components or devices supporting longer-term storage of data, such as a ready only memory, hard drive, Flash memory, or optical disc.

The communication interface 220 supports communications with other systems or devices. For example, the communication interface 220 could include a network interface card or a wireless transceiver facilitating communications over the network 102. The communication interface 220 can support communications through any suitable physical or wireless communication link(s). For example, the communication interface can receive a message from a gateway.

The I/O unit 225 allows for input and output of data. For example, the I/O unit 225 can provide a connection for user input through a keyboard, mouse, keypad, touchscreen, or other suitable input device. The I/O unit 225 can also send output to a display, printer, or other suitable output device.

Note that while FIG. 2 is described as representing the server 104 of FIG. 1, the same or similar structure could be used in one or more of the various client devices 106-118. For example, a desktop computer 106 or a laptop computer 112 could have the same or similar structure as that shown in FIG. 2.

FIG. 3 illustrates an electronic device 300 in accordance with an embodiment of this disclosure. The embodiment of the electronic device 300 shown in FIG. 3 is for illustration only and other embodiments could be used without departing from the scope of this disclosure. The electronic device 300 can come in a wide variety of configurations, and FIG. 3 does not limit the scope of this disclosure to any particular implementation of an electronic device. In certain embodiments, one or more of the client devices 106-118 of FIG. 1 can include the same or similar configuration as electronic device 300.

Electronic device 300 is a location acquisition, and tracking device used in detecting a location of objects and persons within an environment. In certain embodiments, electronic device 300 is useable with data transfer applications, such receiving a ping and generating then transmitting a message. The electronic device 300 can be a mobile communication device, such as, for example, a wireless terminal, a desktop computer (similar to the desktop computer 106 of FIG. 1), a mobile device (similar to the mobile device 108 of FIG. 1), a PDA (similar to the PDA 110 of FIG. 1), a laptop (similar to the laptop computer 112 of FIG. 1), a tablet (similar to the tablet computer 114), a gateway (similar to the gateway 116 of FIG. 1), a beacon (similar to the beacon 118 of FIG. 1) and the like.

As shown in FIG. 3, the electronic device 300 includes an antenna 305, a radio frequency (RF) transceiver 310, a transmit (TX) processing circuitry 315, a microphone 320, and a receive (RX) processing circuitry 325. In certain embodiments, the RF transceiver 310 is a communication unit that includes a BLUETOOTH transceiver, a WI-FI transceiver, ZIGBEE, infrared, and the like. The electronic device 300 also includes a speaker 330, a processor 340, an input/output (I/O) interface 345, an input 350, a display 355, a memory 360, and a sensor(s) 365. The memory 360 includes an operating system (OS) 361, one or more applications 362, and identification information 363 that identifies the electronic device 300.

The RF transceiver 310 receives, from the antenna 305, an incoming RF signal transmitted such as a BLUETOOTH or WI-FI signal from an access point (such as a base station, WI-FI router, BLUETOOTH device) of the network 102 (such as a WI-FI, BLUETOOTH, cellular, 5G, LTE, LTE-A, WiMAX, or any other type of wireless network). The RF transceiver 310 can down-convert the incoming RF signal to generate an intermediate frequency or baseband signal. The intermediate frequency or baseband signal is sent to the RX processing circuitry 325 that generates a processed baseband signal by filtering, decoding, or digitizing the baseband or intermediate frequency signal, or a combination thereof. The RX processing circuitry 325 transmits the processed baseband signal to the speaker 330 (such as for voice data) or to the processor 340 for further processing (such as for web browsing data and remittance).

The TX processing circuitry 315 receives analog or digital data from the microphone 320 or other outgoing baseband data from the processor 340. The outgoing baseband data can include a message, web data, e-mail, or interactive video game data. The TX processing circuitry 315 encodes, multiplexes, digitizes, or a combination thereof, the outgoing baseband data to generate a processed baseband or intermediate frequency signal. The RF transceiver 310 receives the outgoing processed baseband or intermediate frequency signal from the TX processing circuitry 315 and up-converts the baseband or intermediate frequency signal to an RF signal that is transmitted via the antenna 305.

The processor 340 can include one or more processors or other processing devices and execute the OS 361 stored in the memory 360 in order to control the overall operation of the electronic device 300. For example, the processor 340 could control the reception of forward channel signals and the transmission of reverse channel signals by the RF transceiver 310, the RX processing circuitry 325, and the TX processing circuitry 315 in accordance with well-known principles. The processor 340 is also capable of executing other applications 362 resident in the memory 360, such as, one or more applications generating a message or deriving a received signal strength or the like.

The processor 340 can execute instructions that are stored in a memory 360. The processor 340 can include any suitable number(s) and type(s) of processors or other devices in any suitable arrangement. For example, in some embodiments, the processor 340 includes at least one microprocessor or microcontroller. Example types of the processor 340 can include microprocessors, microcontrollers, digital signal processors, application specific integrated circuits, and discreet circuitry.

The processor 340 is also capable of executing other processes and programs resident in the memory 360, such as operations that receive, store, and timely instruct by providing location detection and remote tracking capabilities and processing. The processor 340 can move data into or out of the memory 360 as required by an executing process. In some embodiments, the processor 340 is configured to execute the plurality of applications 362 based on the OS 361 or in response to signals received from eNBs or an operator. In certain embodiments, the processor 340 is configured to instruct memory 360 to store identification information associated with the electronic device 300 or previous location information received from a beacon in an information repository, or both. The processor 340 is also coupled to the I/O interface 345 that provides the electronic device 300 with the ability to connect to other devices, such as client devices 106-118. The I/O interface 345 is the communication path between these accessories and the processor 340.

The processor 340 is also coupled to the input 350 and the display 355. In certain embodiments, the electronic device 300 does not include the input 350, the display 355, or both. For example, when the electronic device 300 is a gateway (similar to the gateway 116 of FIG. 1) the electronic device 300 may not include the input 350 or the display 355, as the gateway receives a ping from a beacon, generates then transmits a message to a server, such as server 104 of FIG. 1.

The operator of the electronic device 300 can use the input 350 to enter data or inputs into the electronic device 300. Input 350 can be a keyboard, touch screen, mouse, track ball, voice input, or other device capable of acting as a user interface to allow a user in interact with electronic device 300. For example, the input 350 can include voice recognition processing thereby allowing a user to input a voice command via microphone 320. For another example, the input 350 can include a touch panel, a (digital) pen sensor, a key, or an ultrasonic input device. The touch panel can recognize, for example, a touch input in at least one scheme among a capacitive scheme, a pressure sensitive scheme, an infrared scheme, or an ultrasonic scheme. Input 350 can be associated with sensor(s) 365 and/or a camera by providing additional input to processor 340. The input 350 can also include a control circuit. In the capacitive scheme, the input 350 can recognize touch or proximity. The display 355 can be a liquid crystal display (LCD), light-emitting diode (LED) display, optical LED (OLED), active matrix OLED (AMOLED), or other display capable of rendering text and/or graphics, such as from websites, videos, games, images, and the like. In certain embodiments, electronic device 300 does not include input 350 or display 355 or both.

The memory 360 is coupled to the processor 340. Part of the memory 360 could include a random access memory (RAM), and another part of the memory 360 could include a Flash memory or other read-only memory (ROM).

The memory 360 can include persistent storage (not shown) that represents any structure(s) capable of storing and facilitating retrieval of information (such as data, program code, and/or other suitable information on a temporary or permanent basis). The memory 360 can contain one or more components or devices supporting longer-term storage of data, such as a ready only memory, hard drive, Flash memory, or optical disc. The memory 360 also can contain identification information 363 that includes identification information of the electronic device 300 and an identification parameter of another electronic device similar to the electronic device 300, such as a beacon. Identification information 363 can also contain data received from a beacon. The identification information 363 can include an identification parameter that can be used to identify each gateway. If the electronic device is a stationary, the identification information can also indicate a location of the electronic device 300. For example, the identification information 363 can include an a room number, a geographic location within a medical facility, and the like.

Electronic device 300 further includes one or more sensor(s) 365 that can meter a physical quantity or detect an activation state of the electronic device 300 and convert metered or detected information into an electrical signal. In certain embodiments, sensor 365 includes inertial sensors (such as accelerometers, gyroscopes, and magnetometers), optical sensors, motion sensors, cameras, pressure sensors, altimeter, and the like. For example, sensor 365 can include one or more buttons for touch input, (such as on a headset or the electronic device 300), a camera, a gesture sensor, a gyroscope or gyro sensor, an air pressure sensor, a magnetic sensor or magnetometer, an acceleration sensor or accelerometer, a proximity sensor, a color sensor, a bio-physical sensor, a temperature/humidity sensor, an illumination sensor, an Ultraviolet (UV) sensor, an Infrared (IR) sensor, an ultrasound sensor, an iris sensor, a fingerprint sensor, an Electromyography (EMG) sensor, an Electroencephalogram (EEG) sensor, and the like. The sensor 365 can further include a control circuit for controlling at least one of the sensors included therein. The sensor(s) 365 can be used to determine an orientation and facing direction, as well as geographic location of the electronic device 300. Any of these sensor(s) 365 can be located within the electronic device 300 or another electronic device in communication with the electronic device 300.

Processor 340 can also be connected to a short range communication circuitry 370. The short range communication circuitry 370 can include additional communication interfaces, such as BLUETOOTH, ZIGBEE, infrared, RFID, and the like. In certain embodiments, short range communication circuitry 370 can be a part of the processing circuitry 325 and 315. In certain embodiments, the short range communication circuitry 370 includes Near Field Communication (NFC). NFC can wirelessly transmit and receive data with other NFC devices. In one example, the NFC can be used to transmit or receive a ping from a beacon. The NFC can emit and/or receive a predetermined Radio Frequency (RF) within a predetermined region. The NFC service may include, for example, a terminal mode, a card mode (or NFC card mode), and a Peer-To-Peer (P2P) mode. The terminal mode executes a function of receiving a ping.

Although FIGS. 2 and 3 illustrate examples of devices in a computing system, various changes can be made to FIGS. 2 and 3. For example, various components in FIGS. 2 and 3 could be combined, further subdivided, or omitted and additional components could be added according to particular needs. As a particular example, the processor 340 could be divided into multiple processors, such as one or more central processing units (CPUs) and one or more graphics processing units (GPUs). In addition, as with computing and communication networks, electronic devices and servers can come in a wide variety of configurations, and FIGS. 2 and 3 do not limit this disclosure to any particular electronic device or server. For example, the electronic device 300 can represent a beacon (such as the beacon 118 of FIG. 1), that periodically transmits a signal that includes identification information that can be received by one or more gateways located throughout a medical facility. In another example, the electronic device 300 gateway (such as the gateway 116 of FIG. 1) which can receive a ping from one or more beacons, generate a message and transmit the message to a computing device such as a server (similar to the server 104 of FIG. 1). In another example, the electronic device 300 can be a computer, (similar to the laptop computer 112 or the desktop computer 106) that can communicate with a server (similar to the server 104 of FIG. 1) over a network (similar to the network 102 of FIG. 1), receive user inputs via input 350 and display results on a display such as display 355.

Figure 4:
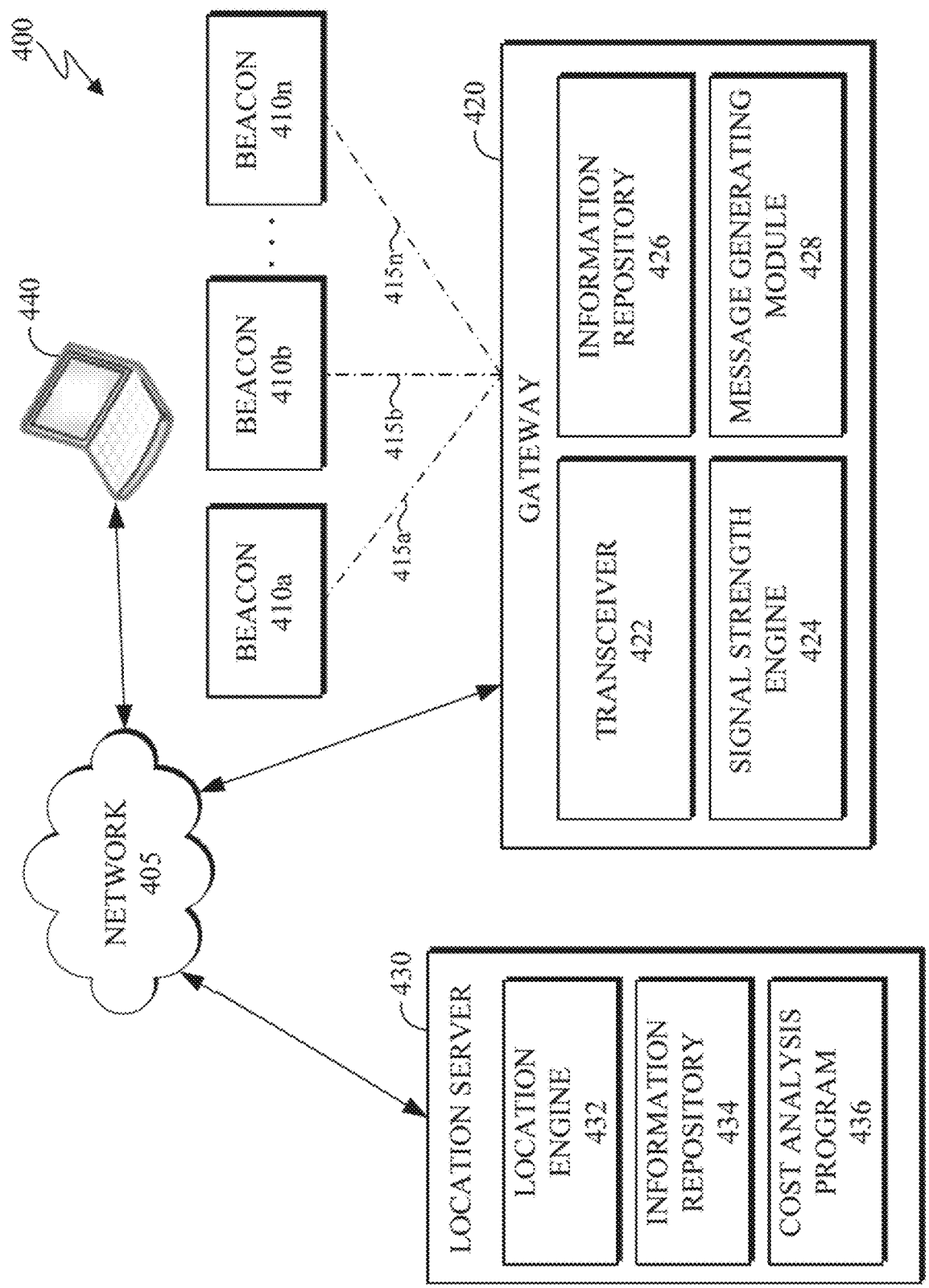
FIG. 4 illustrates an example electronic device in accordance with embodiments of the present disclosure.

FIG. 4 illustrates an example block diagram in accordance with embodiments of the present disclosure. The embodiment of the system architecture 400 shown in FIG. 4 is for illustration only. Other embodiments could be used without departing from the scope of the present disclosure.

System architecture 400 illustrates a high-level overview of an embodiment of the present disclosure to derive costs associated with medical-care of a medical provider to a patient. For example, the system architecture 400 illustrates the ability to locate and track beacon that is associated with a person or equipment and derive a cost based on a beacon's location. Block diagram 400 includes beacon 410a, beacon 410b, through beacon 410n (hereinafter collectively referred to as beacon 410a-410n), in communication with a gateway 420 over short range communication ping 415a, 415b through 415n, respectively (hereinafter collectively referred to as ping 415a-415n). System architecture 400 also includes the gateway 420, a location server 430, and a computer 440 in communication over network 405. In certain embodiments, multiple gateways similar to the gateway 420 are also in communication with the network 405. In certain embodiments, more or less beacons can be in communication with the gateway 420 at any given movement.

The network 405 can be configured similar to network 102 of FIG. 1. The location server 430 can be configured similar to the server 104 of FIG. 1, and the server 200 of FIG. 2. The beacons 410a-410n can be configured similar to the beacon 118 of FIG. 1, and can include internal components similar to that of the electronic device 300 of FIG. 3. The gateway 420 can be configured similar to any of the gateway 116 of FIG. 1 and can include internal components similar to that of the electronic device 300 of FIG. 3.

The network 405 is used to provide communication between the gateway 420, the location server 430, and the computer 440. The network 405 can be a short range communication network, personal area network (PAN), Local Area Networks (LANs), Wireless Local Area Networks (WLANs), the Internet, the Public Switched Telephone Network (PSTN), WAN such as public cellular service as well as other wireless networks. The network 405 may also be the Internet, representing a worldwide collection of networks and gateways that use Transmission Control Protocol/Internet Protocol (TCP/IP) protocols to communicate with one another. The network 405 can include a variety of connections, such as, wired, wireless or fiber optic connections The beacons 410a-410n represents any number of beacons used to track individuals and equipment. In certain embodiments, individuals include patients, medical providers, and staff. In certain embodiments, the equipment includes mobile medical equipment, such as mobile X-ray machines, an electrocardiogram (EKG) machine, a mobile specimen testing (phlebotomy blood draw cart), and the like. Each beacon 410a-410n, such as 410a, is configured to be affixed to an individual or mobile equipment for tracking and monitoring the location of the individual or mobile equipment. Each beacon 410a-410n can transmit a ping that is received by the gateway 420. The ping is a short range communication burst that includes the identification information such as an identification parameter of the beacon that transmitted the ping. For example, the gateway 420 can identify when a specific beacon is near, such as beacon 410a, based on the identification parameter that is included in the ping from the beacon 410a. For example, each beacon 410a-410n can transmit a signal, such as a ping 415a-415n, respectively. In certain embodiments, each beacon 410a-410n can include a power source such as a battery, to power and emit each ping. In certain embodiments, each beacon 410a-410n emits a ping passively in response to passing near a gateway, such as the gateway 420.

In certain embodiments, the beacon 410a-410n can be affixed to mobile equipment, such as a portable medical device. In certain embodiments, the beacon 410a-410n can be associated with an individual. For example, beacon 410a can be affixed to the badge of a medical provider, while beacon 410b is affixed to a wristband worn by a patient. Beacon 410b can be a sticker attached to the wristband. In another example, beacon 410c can be associated with a mobile device of a user, such as a smart phone or a medical device, such as a mobile heart rate monitor.

In certain embodiments, each beacon 410a-410n includes a communication unit configured to transmit a short range communication such as NFC, BLUETOOTH, RFID and the like. In certain embodiments, each beacon 410a-410n includes a RFID tag, where the RFID reader can be the gateway 420. The RFID tag can be passive, active, or battery-assisted passive. For example, an active tag has an on-board battery and periodically transmits its identification parameter via a signal such as pings 415a-415n. A battery-assisted passive tag has a small battery on board and is activated when in the presence of an RFID reader. A passive tag includes no battery; rather, the tag uses the radio energy transmitted by the reader. When the tag is in range of an RFID reader, the tag can transmit the identification parameter of the respective beacon.

In certain embodiments, each beacon is configured to transmit the ping 415a-415n at predetermined time intervals. In certain embodiments, each beacon is configured to transmit the ping 415a-415n when each beacon is within proximity to the gateway 420. Each ping 415a-415n can be a similar power or frequency to allow the signal strength engine 424 (discussed in greater detail below) to derive a signal strength parameter assorted with each received ping.

The signal strength parameter allows the location engine 432 (discussed in greater detail below) to compare two or more received pings to identify a stronger ping. For example, if beacon 410a transmits ping 415a that is received by two gateways, the location engine 432 can identify the stronger signal strength parameter (as derived by the signal strength engine 424) and assign the location of the beacon 410a as the location of the gateway that received the stronger ping 415a.

Each of the beacons 410a-410n are configured for one way or two way communication. If beacon 410a-410n is configured for one-way communication, then each beacon 410a-410n transmits the identification parameter in a signal such as ping 415a-415n respectively. If beacon 410a-410n is configured for two-way communication, then each beacon 410a-410n transmits the identification parameter in a signal such as ping 415a-415n respectively, as well as capable of receiving instructions from the gateway 420. The instructions can change parameters and configurations of the particular beacon. For example, instructions can include one or more: (i) post configuration changes; (ii) maintenance tasks; (iii) instructions to perform a self-diagnostic test and transmit the results; (iv) re-flash the beacons with a set of new firmware, such that the a particular beacon 410a-410n is firmware-over-the-air capable, and the like. It is noted that a portion of the beacons 410a-410n can be configured for one-way communication, while another portion of the beacons 410a-410n can be configured for two-way communication.

In certain embodiments, each beacon 410a-410n has two states: a dormant state and an active state. In the dormant state, each beacon 410a-410n is powered down to reserve power. In the active state, each beacon 410a-410n transmits the signal such as ping 415a-415n to a gateway, such as the gateway 420.

In certain embodiments, beacon 410a-410n can also transmit a status parameter. The status parameter indicates whether the beacon is associated with a patient or a staff member. If the beacon is associated with a patient, the status parameter can include a confidential value that is associated with the patient. The confidential value allows a server to relate the beacon to a particular patient. If the beacon is associated with a staff member such as a medical provider, medical technician, and the like, then the status parameter can include information associated with the staff member. A medical provider can include a doctor, a nurse, a physician's assistant, a nurse practitioner, a pharmacist, a therapist such as a physical therapist, an occupational therapist, a respiratory therapist, a speech therapist, and the like. Each staff member may have a unique salary that is associated with the cost analysis program 436 or maintained in information repository 434 or both. In certain embodiments, the status parameter is a beacon identifier. The beacon identifier can be a unique value for each beacon. The beacon identifier can identify each beacon. For example, an information repository can contain a database that indicates each person, and equipment that is associated with a particular beacon identification value. The database can indicate the status parameter of the beacon so the beacon does not transmit both a beacon identifier and a status parameter.

The gateway 420 represents one or more electronic devices that can be used to communicate with each of the beacon 410a-410n via the ping 415a-415n and the location server 430. Although the block diagram 400 only illustrates a single gateway 420, it is noted that multiple gateways can be utilized.

In certain embodiments, the gateway 420 is located in a stationary position with a structure such as a hospital building, a medical facility, medical provider's office, and the like. Each gateway 420 can be located in a predetermined location within the structure. For example, each room within the structure can include a gateway similar to the gateway 420. In certain embodiments, the gateway 420 is mobile, and traverses through the medical facility.

Each gateway 420 serves as a receiver of a ping, such as ping 415a-415n, for tracking each beacon 410a-410n. Each gateway 420 can generate and transmit a message to the location server 430. The message can indicate the location of each beacon 410a-410n. For example, when the gateway 420 receives a ping, such as ping 415a, the gateway can generate a message and transmit the message to the location server 430, over network 405. The gateway 420 includes a transceiver 422, a signal strength engine 424, an information repository 426, and a message generating module 428.

The transceiver 422 of the gateway 420 provides for both short range communication and long range communication. For example, the transceiver 422 provides communication between the gateway 420, the location server 430, as well as each beacon 410a-410n. In certain embodiments, the gateway 420 is configured for two-way communication. For example, the gateway 420 can receive a ping 415a-415n from each beacon 410a-410n and transmit a generated message to the location server 430. The gateway 420 is also capable of receiving instructions from the location server 430. In certain embodiments, the gateway 420 can receive instructions from the location server 430 and forward the received instructions to one or more beacons such as beacon 410a. In certain embodiments, the transceiver 422 can be an RFID reader. In certain embodiments, the transceiver 422 can include short range communication circuitry (similar to short range communication circuitry 370 of FIG. 3) such as BLUETOOTH, NFC, ZIGBEE, and the like. The transceiver 422 can also include components that provide for communication to the Internet or a private network or both, through WI-FI.

In certain embodiments, the ping 415a, between the beacon 410a and the gateway 420, represents a short range communication. The ping 415a occurs when the beacon 410a is in proximity to the gateway 420. For example, the beacon 410a can be located within a predefined distance from the gateway 420 allowing communication of occur between the beacon 410a and the gateway 420. In another example, the beacon 410a can emit a ping such as ping 415a, regardless of the gateway 420 is able to receive the ping 415a. The ping 415a can also occur when the gateway 420 transmits received instructions or from location server 430, such as configuration changes.

Signal strength engine 424 derives a signal strength parameter associated a received ping, such as pings 415a-415n. For example, signal strength engine 424 measures the power present in a received radio signal of a received ping. The derived signal strength parameter provides a value as to the distance the beacon 410a is from the gateway 420. For example, when multiple gateways are located in close proximity, it is possible for more than one gateway to receive the ping 415a from beacon 410a. Therefore, each signal strength engine 424 can derive the signal strength parameter that indicates an approximate distance the beacon 410a is from each gateway. Based on the derived signal strength parameter, the location server 430 can identify the location of the beacon based on identifying which signal strength parameter is stronger, and assigning the location of the beacon to that of the location of the gateway that transmitted the message. That is, when the location server 430 receives a message from multiple gateways, the location server 430 can assign the location of the beacon 410*a* as the location of a specific gateway that transmitted the message with the identified strongest signal strength parameter. This example is discussed further with reference to FIG. 5, below.

The information repository 426 represents any structure (s) capable of storing and facilitating retrieval of information (such as data, program code, or other suitable information on a temporary or permanent basis). The information repository 426 is capable of saving location information received from ping 415*a*-415*n*. In certain embodiments, the information repository 426 is capable of saving beacon identification parameters associated with each beacon that transmitted a ping to the gateway 420. For example, the information repository 426 can maintain the beacon identifier and a time stamp associated with the received ping. In certain embodiments, the information repository 426 includes an identification parameter associated with the gateway 420. For example, in a structure (such as a hospital building, a medical facility, medical provider's office, and the like) that includes multiple gateways, the identification parameter associated with each gateway can correspond to a location within the structure. In certain embodiments, the identification parameter associated with the gateway 420 is the actual location within the structure.

Message generating module 428 generates a message in response to the gateway 420 receiving a ping, such as ping 415*a* from beacon 410*a*. Message generating module 428 generates a message that includes the beacon identifier of the beacon that transmitted the received ping. For example, when beacon 410*a* transmits ping 415*a*, the gateway 420 receives beacon identifier that is used to identifier the beacon 410*a*. Once the gateway 420 receives beacon identifier of the beacon 410*a*, the message generating module 428 generates a message that includes the beacon identifier of the beacon 410*a*, the identification parameter of the gateway 420, and the derived signal strength parameter of the received ping 415*a*. In certain embodiments, the message also includes a time stamp of the received ping 415*a*.

In certain embodiments, the message generating module 428 is capable of reducing the number of messages the gateway 420 transmits to the location server 430. That is, if the beacon 410*a* repeats a broadcast every time it is in proximity to the gateway 420, or the beacon 410*a* repeats a broadcast at a predetermined interval, the message generating module 428 can prevent the transceiver 422 of the gateway 420 from transmitting a message each time the gateway 420 receives the ping 415*a* from beacon 410*a*. For example, the message generating module 428 can employ an age criteria, such as a time window, to reduce the number of transmission by the gateway 420. A time window limits the number of transmissions within a given period of time. For example, if the gateway 420 receives multiple broadcast messages from the same beacon within a specified period of time, then the message generating module 428 can instruct the transceiver 422 to transmit the first received message to the location server 430 and not send the reminder of the messages until the period of time expires. That is, the message generating module 428 transmits a single broadcast.

The location server 430 can represent one or more local servers, one or more tracking device servers, or one or more asset management servers. The location server 430 can be a web server, a server computer such as a management server, or any other electronic computing system capable of sending and receiving data. In certain embodiments, the location server 430 is a "cloud" of computers interconnected by one or more networks, where location server 430 is a computing system utilizing clustered computers and components to act as a single pool of seamless resources when accessed through network 405. The location server 430 can include a location engine 432, an information repository 434, and a cost analysis program 436.

The location server 430 can include a communication interface (such as the communication interface 220 of FIG. 2) that supports communications with other systems or devices. For example, the communication interface could include a network interface card or a wireless transceiver facilitating communications over the network 405. The communication interface can support communications through any suitable physical or wireless communication link(s). For example, the communication interface can allow the location server 430 to receive a message from the gateway 420. In certain embodiments, the location server 430 transmits reconfiguration data to the gateway 420. The reconfiguration data allows the gateway 420 to reconfigure one or more beacons 410*a*-410*n*, when the beacons are configured for wo-way communication. The reconfiguration can include how often a beacon 410*a*-410*n* transmits a ping 415*a*-415*n* to the gateway 420. The communication interface can allow the location server 430 to communicate with additional servers such as the servers of FIG. 6 and described in greater detail below.

Location engine 432 identifies the location of a beacon. In certain embodiments, location engine 432 identifies the location of a beacon such as beacon 410*a*, based on the identification parameter of the gateway that transmitted the message and the signal strength parameter of ping 415*a* as derived by the gateway 420. The location server 430 receives a message from one or more gateways, such as gateway 420. The message can include an identification parameter of the gateway, a beacon identifier of the beacon that sent the ping to the gateway, and a signal strength parameter of the ping from the beacon to the gateway 420. For example, when a single gateway 420 receives ping 415*a* from the beacon 410*a*, then the location engine 432 identifies the location of the beacon as the location of the gateway 420. In certain embodiments, the location engine 432 identifies a location of a beacon, when multiple gateways receive the ping and transmit a message that includes the beacon identifier from same beacon 410*a*. For example, when multiple gateways receive the same ping 415*a* from the beacon 410*a*, it could appear that the beacon is in multiple locations simultaneously. The signal strength parameter is beneficial to the location engine 432 in this scenario. The location engine 432 utilizes the signal strength parameter to identify a single location for a particular beacon. For instance, two or more gateways (such as gateway 420*a* and 420*b*, not shown but similar to the gateway 420) can receive the same ping 415*a* from the beacon 410*a*. The gateways 420*a* and 420*b* each generate a message that includes the derived the signal strength parameter, each gateways respective identification parameter and the beacon identifier. If each gateway 420*a* and 420*b* is stationary at a predetermined location (based on the identification parameter of each gateway), then the location engine 432 first confirms that each message includes the same beacon identifier. In certain embodiments, the location engine 432 also confirms that each message includes a similar time that the ping was received via the same time stamp. By confirming the beacon identifier, the time stamp, or both, the location engine 432 is able to affirm that the same beacon emitted a ping that was received by both gateways at approximately the same time.

Thereafter the location engine 432 compares the received strength parameter from gateway 420a and gateway 420b. Location engine 432 can determine which signal strength parameter is stronger, and assigned the location of the beacon 410a as the location of the gateway that transmitted the message that included the stronger signal strength parameter. That is, once the location engine 432 determines which received message includes the stronger signal strength parameter, the location engine 432 can disregard the weaker message from the respective gateway, and assign the location of the beacon 410a as the location of the gateway that transmitted the message that included the stronger signal strength parameter. This example is discussed further with reference to FIG. 6, below.

In certain embodiments, the location engine 432 reduces noise from a received signal. For example, the location engine 432 passes each received signal strength parameter through a low-pass filter in order to eliminate each signal strength parameter that is outside of a threshold. The low-pass filter removes outliers and anomalies that could cause incorrect location results. Once each the signal strength parameters are passes each the low-pass filter, a portion of the received signal strength parameters are averaged together. In certain embodiments, a predefined number of signal strength parameters are averaged together. For instance, the predefined number of signal strength parameters that are averaged together is ten. When location engine 432 averages a portion of the signal strength parameters it generates a standardization factor. Thereafter the location engine 432 compares each signal strength parameter to the standardization factor of the averaged signal strength parameter. By comparing each newly received signal strength parameter to the standardization factor the location engine 432 can identify stronger and weaker signal strength parameters.

For example, when a stronger signal strength parameter is identified, the location engine 432 identifies that the beacon (that transmitted the ping) is closer to the gateway that transmitted the message that included the stronger signal strength parameter. Therefore, the location engine 432 assigns location of the beacon as the location of the gateway that transmitted the message that included the stronger signal strength parameter.

In certain embodiments, the location engine 432 identifies a location of a beacon based on trilateration, triangulation, or both. Trilateration is the process of determining absolute or relative locations of points by measurement of distances, using the geometry of circles, or spheres. Triangulation is the process of tracing and measuring a series or network of triangles in order to determine the distances and relative positions of points spread over an area. In certain embodiments, based on signal strength parameter, trilateration or triangulation the location engine 432 tracks each beacon 410a-410n as the beacons 410a-410n move throughout the environment.

The information repository 434 can be similar to the information repository 426 of the gateway 420. The information repository 434 represents any structure(s) capable of storing and facilitating retrieval of information (such as data, program code, or other suitable information on a temporary or permanent basis). The information repository 434 can include a memory and a persistent storage. Memory can be RAM or any other suitable volatile or non-volatile storage device(s), while persistent storage can contain one or more components or devices supporting longer-term storage of data, such as a ROM, hard drive, Flash memory, or optical disc. Information repository 434 stores location information of each beacon 410a-410n, based on the location of the gateway that transmitted the message as determined by the location engine 432.

In certain embodiments, information repository 434 also stores rates associated with each location a gateway is positioned within the environment. For example, a gateway, such as gateway 420 can be located in each examination room, in the waiting room, in a procedure room, and the like. The information repository 434 can maintain a log of the identification parameters of each gateway, the location of each gateway, and the rate associated with each gateway, based on the location of each gateway.

In certain embodiments, information repository 434 also stores cost analysis of each beacon. For example, information repository 434 can maintain a log of time stamped events of when a beacon 410a-410n enters and leaves a location. Based on the time duration that a beacon 410a-410n is located within a single location, cost analysis program 436 can assign a cost associated with the duration of time that the beacon 410a-410n is located within the single location.

The cost analysis program 436 analyzes the duration of time that a beacon is located in each location within the environment. The cost analysis program 436 determines a cost associated at each location a beacon is located, based on the cost associated with each room or area of the structure. That is, the cost analysis program 436 can identify actives and assign a cost of each activities based on the time and resources utilized. The cost analysis program 436 provides an indication of the costs associated with medical-care of each patient that is associated with a beacon.

For example, when a patient goes to a doctor's office, the moment the patient enters the facility the person occupies space that prevents another patient from occupying the same space, such as a seat in the waiting room, an exam room, medical equipment, an imaging device, such as an X-Ray machine, and the like. Each interaction the patient has with an employee or a medical provider is time the employee or medical provider is prevented from assisting another person. Therefore, in order to derive costs associated with the medical-care, costs are associated with each location, and interaction a patient has with a medical provider. For example, each cost associated with particular locations can cover rent, salary the provider and staff, medical equipment, procedures, and the like. The cost analysis program 436 can derive a quantity of time the medical provider interacts and treats each patient, coupled with the medical equipment, and procedures that are provided to treat the patient. The cost analysis program 436 can then derive the totality of costs of treating the particular patient.

In certain embodiments, the cost analysis program 436 can derive a cost associated for interaction between a patient and a medical provider. Similarly, the cost analysis program 436 can derive a cost associated with each patient and the medical equipment as well as each patient and medical test interaction. For example, the cost analysis program 436 can link the beacon identifier of a particular beacon with a particular staff member. If the identification parameter of beacon 410b is associated with a particular doctor, then the tracked location and time duration that beacon 410b spends in a particular location are assigned to that particular doctor.

Based on the duration of each interaction a cost can be derived based on the salary of a medical provider, and the cost associated with each location. For example, if two beacons are located at the same location, where beacon 410a is associated with a patient, and the second beacon 410b is associated with a doctor, the cost analysis program 436 can analyze the time duration that beacon 410a and beacon 410b are located in the same location. Based on the cost associated with the location, and the cost of the doctor as indicated by the beacon 410b, the cost analysis program 436 can derive the cost for the interaction. The cost analysis program 436 can then accrue the time duration that the patient associated with the beacon 410a was located in the waiting room, the exam room without the doctor (the beacon 410b) present, as well as the duration of time of any additional interactions the patient (the beacon 410a) participated in (such as an interaction with a nurse, beacon 410c, medical equipment, and the like).

In certain embodiments, the cost analysis program 436 can determine whether a beacon 410a-410n associated with a medical provider is near an electronic device, such as computer 440. In certain embodiments, the cost analysis program 436 is associated with the computer 440 and identifies time duration that specific content is accessed. For example, when a medical provider reviews a patients file, the cost analysis program 436 can associate the time duration that the file is reviewed with the particular patient associated with the file.

Figure 5:
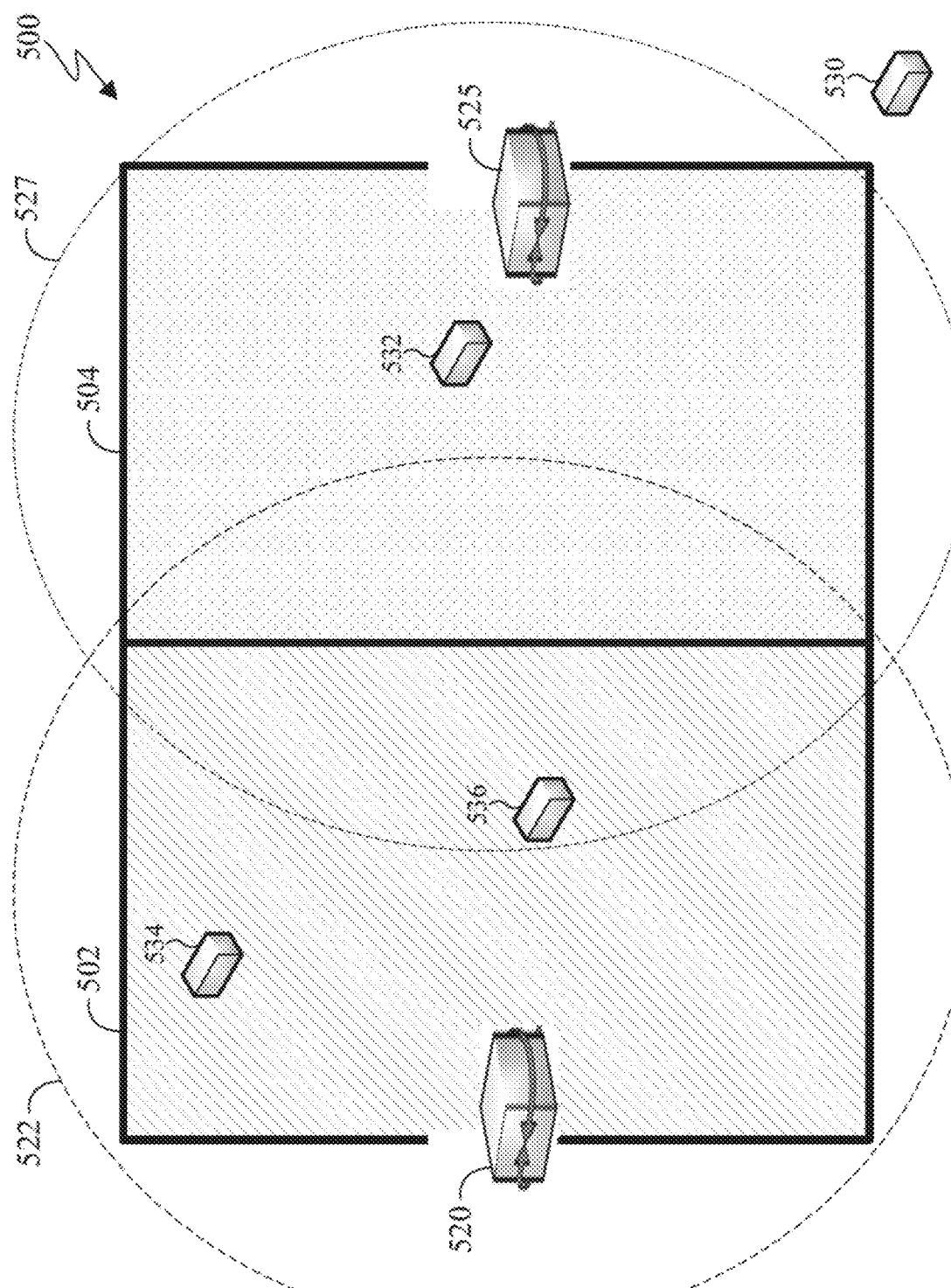
FIG. 5 illustrates an example tracking system in accordance with embodiments of the present disclosure.

Computer 440 is can be similar to the laptop computer 112 or the desktop computer 106 of FIG. 1 or both. Additionally, the computer 440 can include internal components similar to the electronic device 300 of FIG. 3. In certain embodiments, the computer 440 can be an electronic device that can access patient files. For example, the cost analysis program 436 can identify a particular file that is accessed and derive a time duration that the file is accessed. In certain embodiments, computer 440 is a user interface that allows a user to view the cost analysis, the medical resource utilization management, the outcomes, and values that indicate the costs to obtain the outcome FIG. 5 illustrates an example tracking system in accordance with embodiments of the present disclosure. FIG. 5 illustrates an environment 500 depicting a tracking and reporting system of four beacons with two gateways. The embodiment of the environment 500 shown in FIG. 5 is for illustration only. Other embodiments could be used without departing from the scope of the present disclosure.

In certain embodiments, the environment 500 is a medical facility. In certain embodiments, the medical facility of the environment 500 includes two rooms, a first room 502 and a second room 504. The environment 500 also includes a gateway 520, a gateway 525, and four beacons, beacons 530, 532, 534, and 536, located throughout the environment 500. The gateway 520 and the gateway 525 are similar to the gateway 116 of FIG. 1, the electronic device 300 of FIG. 3, and the gateway 420 of FIG. 4. The beacons 530-536 are similar to the beacon 118 of FIG. 1, the electronic device 300 of FIG. 3, and the beacons 410a-410n of FIG. 4.

The beacons 530, 532, 534, and 536 are affixed to an individual or medical equipment and are able to move throughout the environment 500. The gateway 520 is located within the first room 502, and the gateway 525 is located within the second room 504. The gateway 520 includes a communication range of 522 for short range communication, such as BLUETOOTH, WI-FI, ZIGBEE, RFID, or other short range signals. Similarly, the gateway 525 includes a communication range of 527 for short range communication, such as BLUETOOTH, WI-FI, ZIGBEE, RFID, or other short range signals.

The beacon 530 is located external to the rooms 502 and 504 and not within the communication range 522 of the gateway 520 or the communication range 527 of the gateway 525. In certain embodiments, if the beacon 530 transmits a ping, at its illustrated position, then neither the gateway 520 nor the gateway 525 receive the ping. Since the beacon 530 is not within the communication range of 522 or 527, the gateway 520 and the gateway 525 do not receive the ping. Therefore, the beacon 530 cannot be tracked by the cost analysis program 436 of FIG. 4, as the ping of the beacon 530 is not received by the gateway 520 or the gateway 525. In certain embodiments, if the beacon 530 has an RFID tag, the RFID readers, such as the gateways 520 and 525, do not receive the ping as the beacon 530 is not within proximity to the gateways 520 and 525. Since the ping from the beacon 530 is not received by either the gateway 520 or the gateway 525, the beacon 530 cannot be tracked.

The beacon 532 is located within the second room 504 and within the communication range 527 of the gateway 525. The beacon 532 can transmit a ping. The ping can include an identification parameter of the beacon 532. In certain embodiments, the ping can also include a status parameter associated with the beacon 532. The gateway 525 receives the ping as the beacon 532 is within the communication range 527 of the gateway 525. In contrast, the gateway 520 does not receive the ping as the beacon 532 is not within the communication range 522 of the gateway 520. The gateway 525 can determine the signal strength of the received ping from the beacon 532. When the gateway 525 receives the ping, the gateway 525 generates a message. The message includes the identification parameter of the beacon 532, the identification parameter of the gateway 525 and a signal strength parameter of the ping. The gateway 525 then transmits the message to the server, such as the location server 430 of FIG. 4. In certain embodiments, the beacon 532 can transmit a ping at predetermined intervals. Each time a ping is transmitted a gateway that receives the ping generates a message and transmits the message to the location server 430 of FIG. 4. The cost analysis program 436 of FIG. 4 can determine the duration of time that the beacon 532 is located within the room 504 since the ping is transmitted repeatedly at a predetermined interval and a message is generated by the gateway 525 for each received ping. The cost analysis program 436 of FIG. 4 can determine the duration of time that the beacon 532 is located within the room 504 since a message is transmitted from the gateway 525 to the location server 430. Upon the cessation of the messages from the gateway 525 that include the identification parameter associated with the beacon 532, the cost analysis program 436 of FIG. 4 can determine an approximate time the beacon 532 left the room 504. As a result, the cost analysis program 436 can determine an approximate time duration that beacon 532 was within the room 504.

Similarly, the beacon 534 is located within the room 502 and within the communication range 522 of the gateway 520. The beacon 534 can transmit a ping. The ping can include an identification parameter of the beacon 534. In certain embodiments, the ping can also include a status parameter associated with the beacon 534. The gateway 520 receives the ping from the beacon 534 since the beacon 534 is within the communication range 522 of the gateway 520. The gateway 525 does not receive the ping from the beacon 534 as the beacon 534 is not within the communication range 527 of the gateway 525. When the gateway 520 receives a ping, it can determine signal strength of the received ping from the beacon 534. Additionally, the gateway 520 can generate and transmit a message for each received ping. The message can include the identification parameter of the beacon 534, the identification parameter of the gateway 520 and a signal strength parameter of the ping.

The gateway 520 then transmits the message to the server, such as the location server 430 of FIG. 4.

The beacon 536 is located within room 502, similar to that of the beacon 534. The beacon 536 is located within the communication range 522 of the gateway 520 as well as the communication range 527 of the gateway 525. Therefore, when the beacon 536 transmits a ping (that includes identification information of the beacon 536), the ping can be received by the gateway 520 and the gateway 525. In certain embodiments, the ping can also include a status parameter associated with the beacon 536. In response to the beacon 536 transmitting a ping, the gateway 520 and the gateway 525 both receive the ping. In response to receiving a ping from the beacon 536, the gateway 520 can determine the signal strength of the received ping. Thereafter the gateway 520 generates a message that includes the identification parameter of the beacon 536, the identification parameter of the gateway 520 and a derived signal strength parameter of the ping. The gateway 520 then transmits the message to the server, such as the location server 430 of FIG. 4. Similarly when the gateway 525 receives a ping, the gateway 525 also determines the signal strength of the received ping from the beacon 536. Thereafter the gateway 525 generates a message that includes the identification parameter of the beacon 536, the identification parameter of the gateway 525 and a signal strength parameter of the ping. The gateway 525 then transmits the message to the server, such as the location server 430 of FIG. 4. The location engine 432 of the location server 430, analyzes the message received from the gateway 520 and the message received from the gateway 525. In particular the location engine 432 identify that the same beacon transmitted a ping that was received by two gateways at approximately the same time. For example, the location engine 432 identifies that the gateway 520 and the gateway 525 both received the same ping within a predetermined time interval based on the time stamp of the received ping. The location engine 432 can then compare the derived signal strength parameter received from the gateway 520 to that of the derived signal strength parameter received from the gateway 525. Since the beacon 536 is closer to the gateway 520 than the gateway 525, the signal strength parameter as derived by the gateway 520 is stronger than the signal parameter as derived by the gateway 525. Therefore, the location engine 432 assigns the location of the beacon 536 within the room 502.

Figure 6:
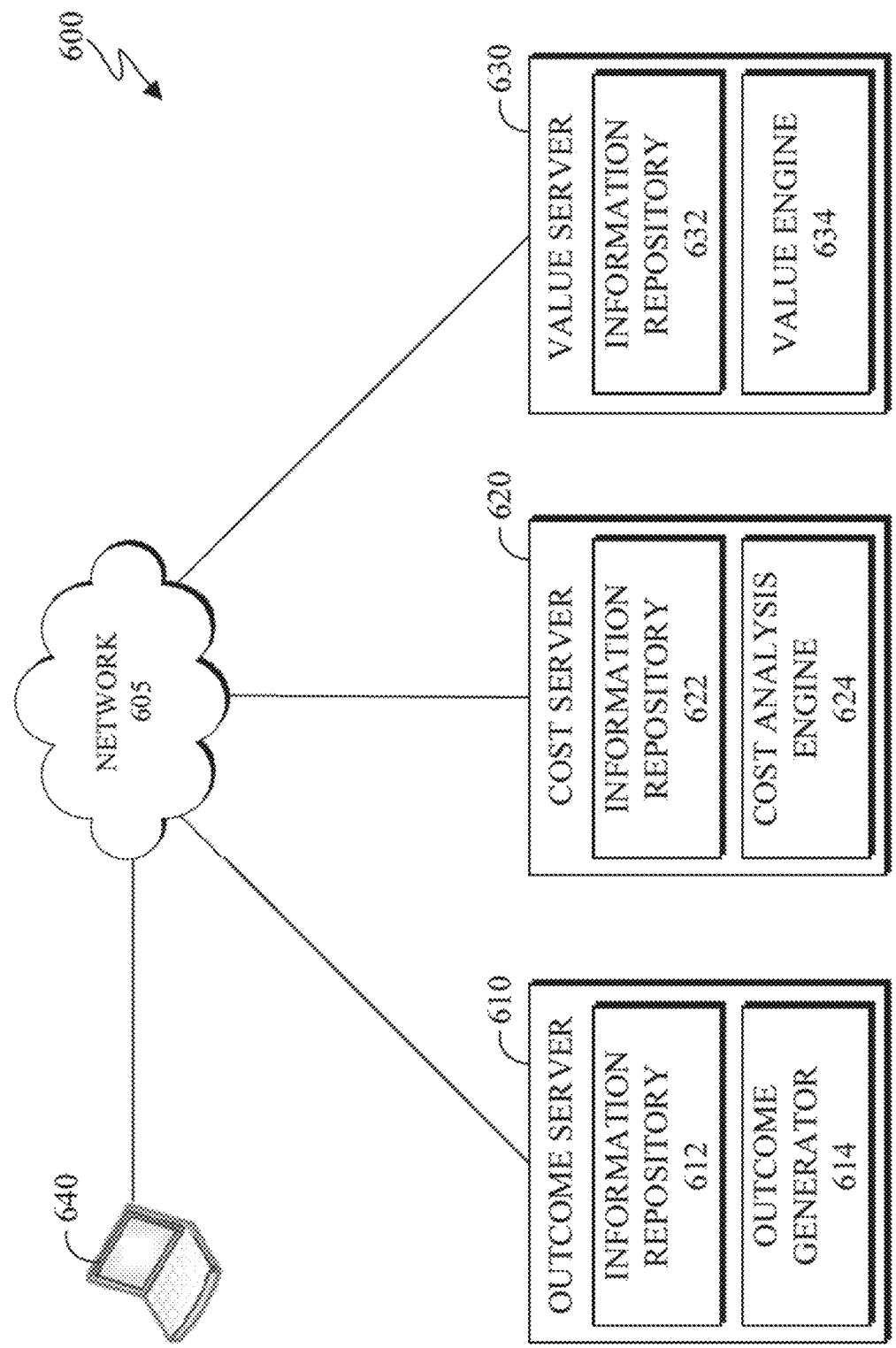
FIG. 6 illustrates an example electronic device in accordance with embodiments of the present disclosure.

FIG. 6 illustrates an example block diagram 600 in accordance with embodiments of the present disclosure. The embodiment of the block diagram 600 shown in FIG. 6 is for illustration only. Other embodiments could be used without departing from the scope of the present disclosure. The block diagram 600 illustrates a high-level overview of an embodiment of the present disclosure to derive value associated with medical-care of a medical provider to a patient. For example, the block diagram 600 illustrates the ability to a value for received medical-care based on the costs accrued to achieve the outcome. The block diagram 600 includes an outcome server 610, a cost server 620, a value server 630, and a computing device 640 all in communication via network 605.

The network 605 can be similar to the network 102 of FIG. 1 and the network 405 of FIG. 4. The outcome server 610, the cost server 620, and the value server 630 can be configured similar to the server 104 of FIG. 1, and can include internal components similar to the server 200 of FIG. 2. The outcome server 610, the cost server 620, and the value server 630 can be similar to the location server 430 of FIG. 4. For example, the cost server 620 and the location server 430 are the same. In certain embodiments, the outcome server 610, the cost server 620, and the value server 630 can be included in a single server. In certain embodiments, the functionality of two or three of the servers 610, 620, and 630 can be combined and included in a single server. In certain embodiments, the outcome server 610, the cost server 620, and the value server 630 represent a "cloud" of computers interconnected by one or more networks (such as network 605), where the servers 610, 620, and 630 are a computing system utilizing clustered computers and components to act as a single pool of seamless resources when accessed. The computing device 640 can be similar to any of the client devices 106-114 of FIG. 1, and include internal hardware similar to that of the server 200 of FIG. 2 and the electronic device 300 of FIG. 3.

In certain embodiments, the network 605 includes a larger networking environment. For example, the network 605 can be used for communication between the outcome server 610, the cost server 620, the value server 630, and the computing device 640. The network 605 is also able to provide a communication medium between the gateways and the beacons, similar to those discussed above with respect to FIG. 4 and FIG. 5. For example, the network 605 can be connected to an information repository (i.e., a database) that contains historical data pertaining to messages transmitted from the gateways to the location server 430.

In certain embodiments, the network 605 represents a "cloud" of computers, servers, or both, that are interconnected by one or more networks, where the network 605 is a computing system utilizing clustered computers and components to act as a single pool of seamless resources when accessed. In certain embodiments, the network 605 represents a wireless network that can range in size from Near Field Communication (NFC) to Local Area Networks (LANs) to wide area networks (WAN). In certain embodiments, the network 605 provides access to the Internet or other remote networks.

The network 605 can also be connected to additional servers that are not shown in the block diagram 600. For example, patient profiles (including patient demographics), information associated with a medical facility's billing department and account receivables, can send and receive information over network 605 to at least one of the outcome server 610, the cost server 620, and the value server 630.

The outcome server 610 can generate surveys, receive surveys, identify locations of a user to derive an outcome, and analyze outcome values associated with medical-care that is provided by a medical provider to a patient. In certain embodiments, outcomes are generated by a medical provider and include empirical data associated with the care and rehabilitation of the patient. In certain embodiments, outcomes are generated by a patient. Patient based outcomes can originate from surveys that are filled out by a patient. Outcomes can be classified based on therapeutic areas such as gastroenterology, muscular skeletal, cardiology, oncology, podiatry, pediatric, respiratory (pulmonology), hematology, rheumatology, urology, neurology, endocrinology, immunology, infection disease, dermatology, woman's health, nephrology, to name a few. The outcomes can provide indicators that reveal areas where medical-care and intervention can be improved, identify variations of medical-care from provider to provider, provide evidence of medical-care that works best in relation to certain types of patients under particular circumstances, as well as an ability to compare the effectiveness of various treatments and procedures. The outcome server 610 includes an information repository 612 and an outcome generator 614.

The information repository 612 can be implemented using any architecture known in the art, such as a relational database, an object-oriented database, one or more tables, or a combination thereof. In certain embodiments, the information repository 612 is external to the outcome server 610. The information repository 612 stores data associated with patient profiles, medical facility profiles, medical provider profiles, as well as outcome reports and results. In certain embodiments, the patient profiles, the medical facility profiles, and the medical provider profiles can be maintained in one or more separate information repositories external to the outcome server 610. The information repository 612 can maintain surveys that are filled out by patients, medical providers, or both. The surveys can provide an indication as to one or more outcomes.

For example, almost every ailment, disease, injury, and the like that a patient can suffer has some outcome measurement associated therewith. Similarly, medical interventions performed or administered by medical providers can have outcome measurement associated therewith. The outcome measurement can be a survey filled out by the patient that indicates (i) whether the patient is happy with the medical provider, (ii) whether the patient has full use of the body part following the ailment, (iii) whether medical-care was provided in a timely manner, (iv) how close is the patient to being fully recovered (such as before the injury, ailment, disease occurred), and the like. The outcome measurement can be a survey filled out by the medical provider that provides diagnostic and measured values associated with the recovery. For example, if the patient broke a particular portion of a bone, the outcome can relate to the usability of the muscular-skeletal structure of broken bone and surrounding areas. For instance, a range of motion of a patients can be measured and compared to a normalized range of motion of the same body part but without the injury, the normalized range of motion if medical-care was not provided, or if a different type of medical-care was provided. In another example, relating to orthopedic outcomes, a medical provider can fill out the MODIFIED CINCINNATI RATING SYSTEM or the TEGNER LYSHOLM KNEE SCORING SCALE that provide outcome based scores for the knee of a user. Another outcome score is the DISABILITIES OF THE ARM, SHOULDER, AND HAND (DASH) score, and the BACK PAIN INDEX. Another outcome score is the OXFORD JOINT SCORE that is used for joint replacements. The MICHIGAN HAND QUESTIONNAIRE score is sued to derive outcome scores associated with hand injuries. In another example, a psychological outcome can be based on the DISTRESS AND RISK ASSESSMENT METHOD (DRAM). Regardless of the type or source of the outcome, the information repository 612 maintains the outcomes.

The outcome generator 614 generates surveys that can be filled out by patients and medical providers. In certain embodiments, the outcome generator 614 is not included in the outcome server 610. The outcome generator 614 can receive an indication that a particular patient is discharged from the hospital, completed an office visit with a medical provider, or is currently undergoing medical treatment. In response to receiving the indication, the outcome generator 614 can generate a survey based on the type of treatment, ailment disease, medical-care that is being or was provided to a patient. In certain embodiments, the outcome generator 614 generates specialized surveys that are dependent on the condition being treated. The outcome generator 614 can generate outcomes that are specific to certain conditions, such as, for example, a particular type of arthritis at a specific portion of the thumb. In certain embodiments, the outcome generator 614 generates a single survey regardless of the medical-care provided to the patient. When a survey is generated, the outcome generator 614 can transmit the survey to the patient via a communication interface, similar to the communication interface 220 of FIG. 2. The communication interface can transmit the survey via postal mail, electronic mail, phone calls, and the like based on biographical information contained within the patient file. The outcome server 610 can then receive the survey filled out by the patient via a communication interface, similar to the communication interface 220 of FIG. 2. In certain embodiments, the outcome generator 614 can also generate and transmit a survey to be filled out by the medical provider.

In certain embodiments, the outcome generator 614 can identify particular outcomes based on the geospatial location of a patient as identified by the location server 430. For example, if the patient goes from the operating room of a hospital to a morgue, the outcome generator 614 identifies the outcome of the surgery is death, yielding a low or null outcome score. In contrast, if the patient goes from the operating room of a hospital to a recovery room of the hospital and is subsequently discharged and leaves the hospital, the outcome generator 614 identifies the outcome of the surgery as successful and can generate a high outcome score. Further, the outcome generator 614 can adjust the outcome score based on the time the patient remains in the hospital following surgery as compared to national averages or standard practices. For example, based on the type of surgery a patient typically spends two days in the hospital, but a particular patient spends longer, the outcome generator 614 can reduce the outcome due to the extended recovery needed in the hospital. In another example, the outcome generator 614 can generate an outcome based on the number of return visits the patient undertook to resolve the ailment. For example, based on the medical code, if the patient returned three times to the medical facility and only a single visit is the national standard, a low outcome score is generated. In another example, if the patient is re-admitted to the medical facility within so many days after leaving the medical facility, can generate a low outcome. For instance, readmission can indicate poor effectiveness of the care, poor communication and instruction that the patient is to follow when the patient is discharged from medical-care, a secondary infection caused by the prior visit to the medical facility, and the like. In another example, the outcome generator 614 can identify whether a patient's length of stay in the hospital is longer or shorter than a national average, and adjust the outcome score accordingly (provide a better outcome score for a shorter stay and a worse outcome score for a longer stay). In another example, the outcome generator 614 can adjust the outcome score based on movement of the patient following a surgery or medical procedure. For instance, if the patient had knee surgery, and is walking later that day, the outcome score can reflect the number of steps the patient walked each day to show improvement.

The outcome generator 614 can also derive outcomes based on a patient's condition. For example, if a patient suffers from a blood clot while in a hospital the outcome generator 614 can provide a low outcome score to the hospital as the patient was not treated with the necessary care to prevent blood clots. Similarly, if the patient suffers from a secondary invention following a hospital stay or surgical procedure, the outcome generator 614 can lower the outcome of the facility. In certain embodiments the outcome generator 614 can adjust the outcome score based on the severity of the secondary invention such as whether out-patient antibiotics, in-patient antibiotics, or surgery are used to resolve the secondary infection.

In certain embodiments, the outcome generator 614 can adjust the outcomes based on demographic and biographic information of the patients. For example, if the patient suffers from a back injury but their job requires the user to sit and work on a computer could cause a delay with respect to a full recovery. In another example, if biographical data of the patient indicates a high propensity for heart disease due to family history, the outcome score can be adjusted to account for genetic issues rather than a simple cure.

The cost server 620 can derive costs associated with medical-care. The costs can be real time costs derived based on the location of the patient, the medical provider, and the equipment. The costs can include billed statements and accounts received. The costs can reflect payments from both the insurance provider as well as the patient. The cost server 620 includes an information repository 622 and a cost analysis engine 624.

The information repository 622 can be implemented using any architecture known in the art, such as a relational database, an object-oriented database, one or more tables, or a combination thereof. In certain embodiments, the information repository 622 is external to the cost server 620. The information repository 622 stores data associated with patient profiles, medical facility profiles, medical provider profiles, as well as outcome reports and results. In certain embodiments, the patient profiles, the medical facility profiles, and the medical provider profiles can be maintained in one or more separate information repositories external to the cost server 620. In certain embodiments, the information repository 612 and the information repository 622 are the same. In certain embodiments, the information repository 434 of FIG. 4 and the information repository 622 are the same.

The information repository 622 maintains rates of each room within the medical facility in which a financial expenditures can accrue. For example, a rate can be associated with the waiting room, an exam room, a medical device room such as an X-ray, a MRI, and an ultrasound room, an operating room, and the like. The information repository 622 can also maintain a log of each location and the time duration that a patient spends in each room within the medical facility. In certain embodiments, the information repository 622 can also maintain a log of the time duration the patient spends with one or more medical providers. Furthermore, the information repository 622 can maintain a log of medical equipment and supplies that are used during the treatment of the patient.

In certain embodiments, the information repository 622 maintains a log of salaries of each employee, staff member, and medical provider. In certain embodiments, the information repository 622 can also store national or local salary averages, or both, based on the employee job title, experience level, and the like. The information repository 622 can also maintain benefits of each employee. By tracking the salaries and benefits, the cost analysis engine 624 (discussed below) can derive costs based on the duration of time each employee spends with a patient. For example, by maintaining a list of salaries, a portion of the salary of the employee can be allocated to each patient's accrued costs, based on the time duration the employee spends with each patient. In another example, if an employee sees ten patients a day and spends five minutes with each patient (totaling 50 minutes a day of patient interaction), the cost analysis engine 624 can derive an approximate cost per patient based on the employees daily salary.

In certain embodiments, the information repository 622 can receive financial billing information from an accounting system. For example, the information repository 622 can receive information associated with the amount billed to an insurance company, the amount collected from the insurance company, the amount billed to the patient, the amount collected from the patient. The amount billed and the amount collected from either the insurance company or the patient may not be the same.

The cost analysis engine 624 can be the same as the cost analysis program 436 of FIG. 4. The cost analysis engine 624 determines costs associated at each location a beacon is located, based on the cost associated with each room or area of the medical facility. The cost analysis engine 624 can identify activities, such as medical treatment and medical-care based on the location of the patient, and the medical provider. The cost analysis engine 624 can then assign a cost of each activity based on the time and resources utilized.

In certain embodiments, the cost analysis engine 624 can manipulate and adjust the information included in the information repository 622. For example, the cost analysis engine 624 can derive the average costs associated with a certain procedure. For instance, based on an identified ailment, intervention, and similar patient demographic data, the cost analysis engine 624 can average the total costs for the intervention as administrated by the medical provider to the patient. The average cost associated with particular interventions can be limited to a certain location, such as a specific medical practice, a specific city, a specific state, a specific region of the country, and the like. In certain embodiments, the cost analysis engine 624 can normalize the costs based on received data. For example, if the government issues a statement stating that a nurse in a particular part of the country should be making a certain salary, the cost analysis engine 624 can adjust the inputted salary of the nurses to the notational standard.

The value server 630 generates a value score that relates cost to an outcome. For example, the value server 630 can generate a value score that is based on the outcome per cost, where cost is the derived costs based on empirical data derived from geographic locations and time durations of the beacons within a medical facility to an achieved outcome. In certain embodiments, the value server 630 can compare one medical intervention to another medical intervention to identify a particular medical treatment of action based on patient outcomes and the costs associated with obtaining each outcome. That is, the value server 630 can derive a value for a single instance of medical-care, as well as compare multiple values to identify particular results. When comparing various outcomes and costs, the value server 630 can associate demographic data of a patient including, age, gender, relative health, and the like. The value server 630 includes an information repository 632 and a value engine 634.

The information repository 632 can be implemented using any architecture known in the art, such as a relational database, an object-oriented database, one or more tables, or a combination thereof. In certain embodiments, the information repository 632 is external to the value server 630. The information repository 632 can store data associated with patient profiles, medical facility profiles, medical provider profiles, outcome reports and results, as well as costs associated with medical-care. In certain embodiments, the information repository 612, the information repository 622, and the information repository 632 or a combination thereof are the same. For example, the information maintained in the information repositories 612 and 622 can be maintained in a single information repository located external or internal of the value server 630.

The value engine 634 derives a value associated with each particular outcome based on previous outcomes and the empirically generated data of costs. In certain embodiments the value engine 634 derives the value based on the outcomes over the costs. For example a value score can be a ratio of the outcome to cost. The outcomes can be based on either generated or received surveys. The outcomes can be based on the on medical instruments that indicate outcomes such as patient measurements and standardized forms (for example the DASH score). The outcomes can be based on the on location data of the patient (such as the duration of time the patient spent in the hospital over or under a normalized stay for a similar medical code, re-admittance, secondary infection, death, and the like). The costs can be the costs derived by the cost server 620 based on the location server 430. The costs can be the collected monetary finds from medical facilities billing department. The costs can be the amount of money billed to a patient or insurance company.

In certain embodiments, the value engine 634 derives a value score that relates the identified cost of the medical-care provided by the medical provider to the patient, to achieve the acquired outcome. For example, for the same ailment, the outcomes can range from the type of medical intervention used, the patient wait time (both in the office visit, and from the onset of the injury to full recover and anything in-between), the rehabilitation/recovery time, level of invasiveness (a surgical incision as compared to laparoscopic/arthroscopic surgery as compared to therapy), medication (including types and duration of medication), and the like. Each of the various medical interventions can have different costs associated therewith. For example, physical therapy is often less expensive than surgery. It is noted that in certain instances, physical therapy can be required after surgery, thereby further increasing the costs associated with surgery. In another example, the time to undergo and recover from surgery can be less than time necessary for medical and therapy interventions. Therefore, based on the desired outcome, different medical interventions can be associated with different costs.

The value engine 634 can analyze the information repository 632 to compare the derived value of each outcome with each cost to identify outcomes with the highest value. In certain embodiments, the value engine 634 can organize each value based on particular outcomes, particular medical code ailments, particular costs incurred, patient demographics such as age, gender, relative health, occupation, and the like. The value score can indicate whether a particular intervention is better based on the outcome to cost ratio. For example, when treating a patient with Carpal Tunnel Syndrome, the value score can indicate whether a brace or surgery is better based on an outcome range of movement following the medical intervention. If the range of movement is the same for both intervention methods (surgery and brace) and the cost for a brace is less, then the value score indicates that a brace is better. If the range of motion is significantly more following surgery (a larger outcome score) and the cost of surgery is larger compared to the cost of the brace, the value score can provide an indication as to how much of an additional range of motion is needed to make surgery a viable option, where the cost is based on historical data based on similar patient demographics and similar medical provider information.

In certain embodiments, the value engine 634 analyzes the outcome scores and divides the outcome score by the costs associated with a particular procedure. For example, if costs associated with an operation are significantly more than costs associated with therapy, but the outcome from the operation is significantly better, then comparing the value score from one the operation with one of therapy indicates that the operation is better. In another example, if costs associated with an operation are significantly more than costs associated with therapy, but the outcome from the operation is slightly better, then comparing the value score from one the operation with one of therapy indicates which medical intervention method is better.

When only the outcome scores are compared to identify which medical intervention method provides the highest outcome, the result does not provide an indication as to the real costs associated with each medical intervention method. By not accounting for the real costs associated with each medical intervention, this method lacks an indication as to whether the additional costs associated with the higher priced medical intervention method adds any appreciable value to the outcome. Similarly, when only the costs are used to indicate certain medical intervention methods are preferred, the result does not account for outcomes and patient well-being. Therefore, embodiments of the present disclosure apply known costs, as derived by the cost server 620 from the beacons associated with each patient and medical provider, such as beacons 410a-410n of FIG. 4, with known outcomes (from the outcome server 610) to identify a value associated with each intervention.

In certain embodiments, each value score can be patient-specific, ailment-specific, intervention-specific, outcome-specific, or demographic-specific. For example, many value scores can be associated with a single medical ailment based on different outcomes being measured. The outcomes being measured can be the time it takes the patient to be seen by a medical provider, time for recovery, patient happiness with the medical provider, and the like. Therefore, an array of value scores can be generated based on the particular outcomes and interventions that are being analyzed. The array can also include various standard deviations such as per patient and averaged based on intervention method, and similar patient demographics, and the like.

A value score generated by the value engine 634 can be a particular score directed to a facility, a medical code, a medical provider, a clinic, a hospital, areas within a hospital (such as the operating room, an intensive care unit, the emergency room, and the like), patient specific, among others. A patient specific value score can be based on measurements for a specific medical condition based on similar demographics that match the actual patient. A medical provider value score is based on the outcomes of a patient but attributable to the intervention performed by the medical provider. For example, if the patient outcome score for a broken arm is based on the DASH questionnaire, the value engine 634 analyzes the DASH score of each patient with similar diagnostic codes, select particular aspects of the DASH score and relates one or more aspects of DASH scores from each patient to the cost of treating each patient. The cost of treating the patient is based on the time the medical provider spends with the patient, the time each patient spends at each location within the medical facility, and the equipment and supplies needed to treat the broken arm (such as an X-ray machine, and supplies and personnel needed to make a cast for the patient).

In certain embodiments, the value score generated by the value engine 634 can be subjective to the end user. For example, the user to select particular outcome scores, particular costs, specific medical codes, and certain patient demographics to generate the value score. For instance, outcome scores can vary drastically from actual range of motion measurements following a knee replacement to whether the patient was happy with the provider. Additional outcome scores can be based on pain level and speed of recover. Outcome scores can also vary based on the type of intervention that the medical provider used to treat the patient. For example, two patients with the same medical code ailment can receive multiple different treatments to resolve or treat the medical code. Outcome scores can also be based on the location of the patient. For example, if the patient is alive or dead, re-admitted to the hospital, moved to a higher level of care (such as an intensive care unit), required emergency surgery, and the like. Costs can also vary. For instance, costs can be based on the salaries of the individual providers or national averages. Costs can also be based on specific locations and rents or national averages. Costs can also be based on the fastest, slowest, or average time a patient is seen and being treated.

In certain embodiments, the value engine 634 can include a value comparison module that is used to compare different treatments, different medical facilities, medical providers, and the like. For example, the value engine 634 can compare the value of treating similar medical codes differently. For example, a patient with a broken arm can receive medical treatment of a cast, physical therapy, surgery, and the like. The value engine 634 can analyze the different outcome scores along with the different costs incurred to achieve each specific outcome to identify a particular course of treatment for the patient, based on the demographics of the particular patient. For example, if the cost of surgery is higher than a cast, but the outcome scores indicate the same range of motion recovery, then the value engine 634 will indicate the a cast yields a higher value score. If the outcome the value engine 634 is analyzing is the speed of recovery then the value engine 634 will indicate whether a cast or surgery yields a higher value score. If the outcome the value engine 634 is analyzing is the invasiveness or pain associated with medical treatment, the value engine 634 can indicate the cast yields a higher value score, as the cast is less invasive than surgery. If the outcome of surgery is slightly better than a cast, but the cost of surgery is significantly more (due to the time of multiple medical providers performing surgery, the time the patient spends in the operating room, the time the patient spends in the recovery room, the time the patient spends with medical providers for follow up appointments following the surgery, and the like), the value engine 634 can indicate which course of treatment is better, based on the demographics of the patient, such as age, weight, gender, job, relative health, and the like. That is, the value engine 634 compares costs with various outcomes associated with each medical intervention to identify a course of treatment. In certain embodiments, the value engine 634 compares costs with various outcomes associated with each medical intervention as well as similar patient demographics to identify a course of treatment.

In certain embodiments, the value engine 634 includes a predictive module that indicates whether adding or removing staff and whether adding or removing equipment from a medical facility will increase or decrease the value score for the particular medical facility. For example, if a medical facility treats a certain number patients a day for a radial head fracture, the cost server can identify the time duration it takes to treat each patient. Treating each patient can include, the patients wait time, medical imaging, a medical provider discussing treatment options with each patient, the actual treatment, and the like. The value engine 634 can indicate whether adding or removing a technician, a nurse, a medical provider, an examination room, medical imaging equipment, and the like will allow the facility to treat more patients, close earlier, reduce wait times, provide better patient care, and the like. For example, if adding an additional medical provider yield's less wait time for patients improving the outcome score of patient satisfaction, then the value score can increase. In another example, if adding an additional medical provider yields more time each medical provider spends with each patient, improving treatment and recovery time, then the value score can increase. If adding an additional medical provider costs the medical facility more money to cover the salary associated with an additional provider, and the increased costs are not offset by increased outcome scores then the value score can decrease.

The computing device 640 is a computing device with a user interface that allows a user to interact with the outcome server 610, the cost server 620, the value server 630 or a combination thereof. The computing device 640 can be located at a medical facility, a billing department of a medical facility, an insurance company, a private residence of a medical provider and the like. In certain embodiments, the outcome server 610 and the computing device 640 are the same. In certain embodiments, the cost server 620 and the computing device 640 are the same. In certain embodiments, the value server 630 and the computing device 640 are the same.

The computing device 640 can automatically populate cost and outcome fields indicating particular outcomes and costs the value engine 634 is to analyze. Thereafter, the computing device 640 can display array of value scores based on the various costs and outcomes from the value engine 634. In certain embodiments, the value engine 634 can access a program stored on the client device and automatically populate the cost and outcome fields from the cost server 620 and the outcome server 610 to generate an array of value scores based on the various costs and outcomes.

The computing device 640 can display the patient's name, and the accumulated costs associated with the treatment of the named patient. In certain embodiments, the patient can be represented by an identification number or code similar to those utilized for patient privacy. The displayed cost can be total costs for the patient accrued for a particular medical code, for a particular ailment, or since the patient started with the medical facility. For example, the cost can represent the entire treatment of care, such as the initial medical visit through any follow up visit associated with the initial visit. In another example, the cost can represent a single office visit. The cost can include the initial visit, and any subsequent surgery or intervention that stemmed from with the initial visit. The cost can be based on the derived cost from the cost server 620, or the location server 430 of FIG. 4. For example, the cost can be based on location and time duration of the patient based on a beacon, such as beacon 410a. The cost can also include the bills sent to the patient or insurance company or both. The cost can include monetary collections from the patient or insurance company or both. In certain embodiments, the cost can be a normalized cost. The normalized cost can be derived by removing variables (such as variables associated with salary, benefits, rent, and the like) and utilize national averages.

The computing device 640 can also display the diagnosis of the patient. In certain embodiments, the computing device 640 also displays a list of various outcomes that are particular to the diagnosis. The outcomes can be based on surveys, instruments (such as the DASH score, the DRAM), and the like. The outcomes can include an overall score, or individual scores.

The user interface of the computing device 640 can allow the user to select one or more costs and one or more outcome scores. If multiple costs or outcome scores are selected, the value engine 634 generates an array of values that are displayed on the user interface. In certain embodiments the computing device 640 includes the value engine 634 and generates and displays the array of values. For example, the array of value scores can be differ based on using different costs, (such as the actual cost, national average cost, a single appointment cost, entire treatment cost, and the like) and different outcomes.

The generated values can then be compared to another patient, or another group of patients as a metric to compare (i) one treatment to another, (ii) one medical facility to another, (iii) different patient demographics, (iv) one provider to another, (v) similar diagnosis and the interventions associated therewith, and the like.

Figure 7:
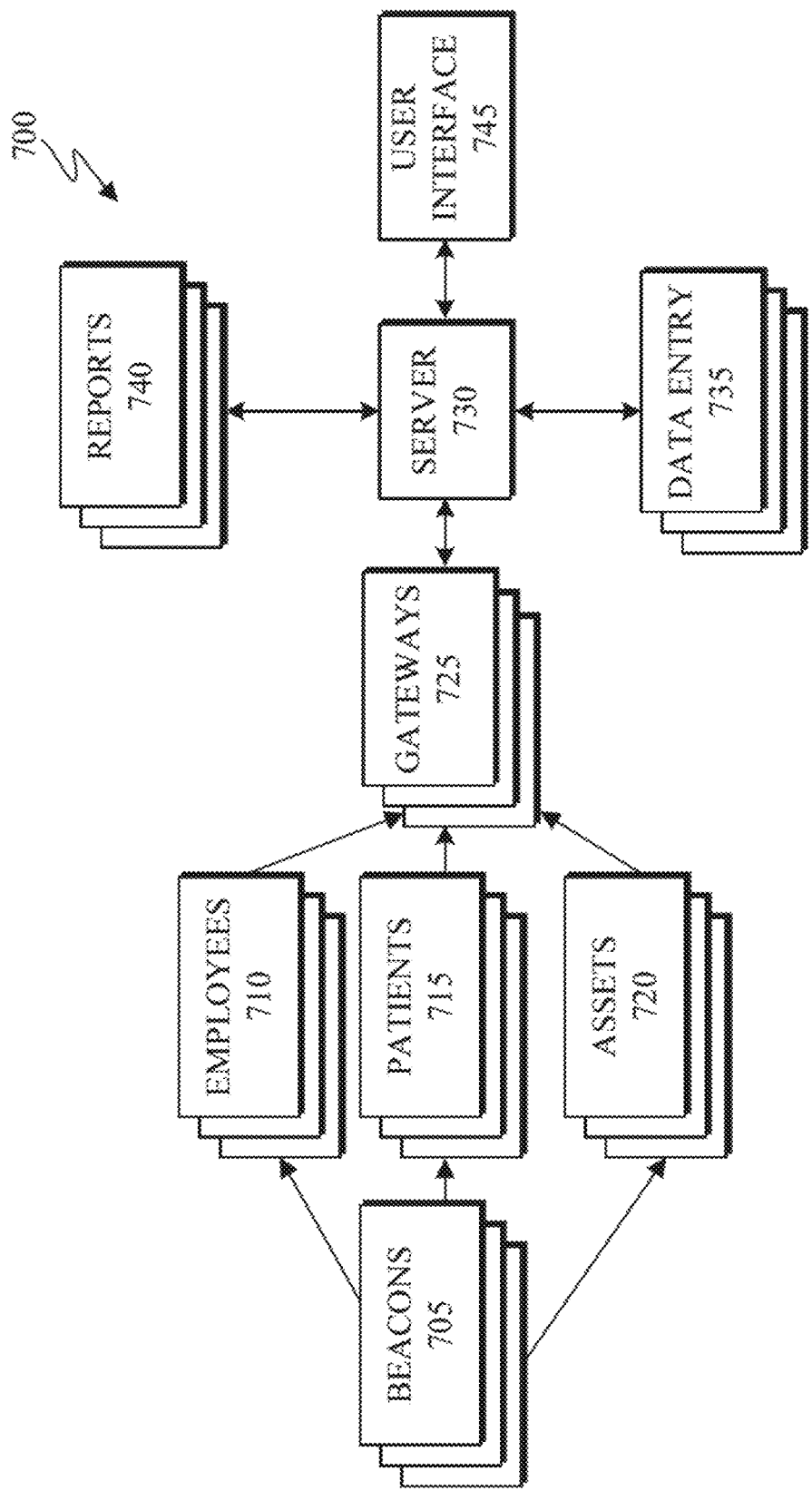
FIG. 7 illustrates a process of gathering and manipulating data to be displayed on a user interface in accordance with embodiments of the present disclosure.

FIG. 7 illustrates a process of gathering and manipulating data to be displayed on a user interface in accordance with embodiments of the present disclosure. FIG. 7 illustrates an example diagram 700 in accordance with embodiments of the present disclosure. The embodiment of the diagram 700 shown in FIG. 7 is for illustration only. Other embodiments could be used without departing from the scope of the present disclosure. Diagram 700 illustrates a high-level overview of an embodiment of the present disclosure to derive value associated with medical-care of a medical provider to a patient. For example, diagram 700 illustrates the ability to derive a value for received medical-care based on the costs accrued to achieve the outcome, and display the derived value on a user interface.

Diagram 700 illustrates that beacons 705 can be associated with employees 710, patients 715, and assets 720 within a medical facility. The beacons 705 can be similar to any of the beacons 410a-410n of FIG. 4. The beacons 705 represent any number of beacons. The employees 710 can represent any number of employees at a medical facility. For example, the employees 710 can be any staff members that have direct or indirect patient interaction, such as a doctor, resident, fellow, physician's assistant, nurse practitioner nurse, therapist, technician, receptionist, and the like The patients 715 represent any number of patients that are receiving medical-care at the medical facility. The assets 720 represents any number of mobile medical equipment such as a medical imaging (including X-Ray machine, ultrasound, and the like), EKG machine, crash cart, lab cart, supply cart, to name a few.

The beacons 705 can be associated with any number of the employees 710, the patients 715, and the assets 720. For example, one of the he beacons 705 can be associated with each of the employees 710, patients 715, and assets 720. For example, the beacons 705 can be issued to each of the employees 710 that are to be tracked throughout the medical facility. Each of the patients 715 can receive one of the beacons 705 when checking into the medical facility. The patients 715 can then return their beacon 705 when the checkout or are discharged. Additionally, one of the beacons 705 affixed to each of the assets 720.

The beacons 705 transmit a signal such as the ping 415a-415n of FIG. 4 to gateways 725. The gateways are similar to the gateway 420 of FIG. 4. The gateways 725 are located throughout the medical facility similar to the gateways of FIG. 5. The gateways 725 receive pings from the beacons 705. In response to receiving a ping from the beacons 705, the gateways 725 generate and transmit a message to a server 730.

The server 730 can represent the location server 430 of FIG. 4, the outcome server 610 of FIG. 6, the cost server 620 of FIG. 6, the value server 630 of FIG. 6, or any combination thereof. For example, the server 730 receives the messages from the gateways 725 and locates each of the beacons 705 throughout the medical facility. Based on the location of the gateways 725, the server 730 is able to assign a location of each of the employees 710, the patients 715, and the assets 720 throughout the medical facility. The server 730 is also able to derive the time deration each of the employees 710, the patients 715, and the assets 720 are located in each location. The server 730 can include an information repository that includes cost per unit of time associated with each location. For example, if one of the patients 715 spends a first period amount of time in the waiting room and a second period of time in an exam room, the server 730 is able to derive a cost for the patient based on the patient's location. Similarly, if one of the employees 710 is a medical provider and is located in the same room as the patient 715 during a third period of time, the server 730 can allocate the time the medical provider spends with the patient and derive the cost for interaction time the medical provider spends with the patient 715. The server can then increase the costs accrued by the patient based on location to include the time the patient spent with the medical provider. In certain embodiments, if one of the patients 715 re-enters to the medical facility after leaving and receives a new beacon 705, the server 730 can relate the identification information of the first beacon to the identification information of the second beacon the patient received.

The server 730 can receive data entry 735 that includes surveys, outcome scores, billing reports, national averages, and the like. The data entry 735 can include the employees 710 salaries, expected hours worked, benefits, rent for the facility and the assets 720, costs associated with maintaining equipment and supplies at the medical facility. The data entry 735 can include the patient's demographic data, and medical history. In certain embodiments, the data entry is automatically inputted into the server 730.

Additionally, the server 730 can receive reports 740 that include surveys, outcome scores, billing reports, national averages, and the like. The reports 740 can include the patient's demographic data and medical history. In certain embodiments, the server 730 generates one or more reports 740, such as an outcome survey. The outcome survey can then be transmitted to the patients 715 to provide an outcome score.

In certain embodiments, the server 730 can include the value engine 634 of FIG. 6 that derives the value score. User interface 745 allows a user to derive a value based on selected outcome scores, and selected costs. The server 730 can then transmit an array of values associated with thee selected outcome scores, and selected costs to be displayed on the user interface 745. In certain embodiments, the server 730 can analyze medical codes, patient demographics and the like to compare different interventions to identify an intervention that yields a larger value score.

Figure 8:
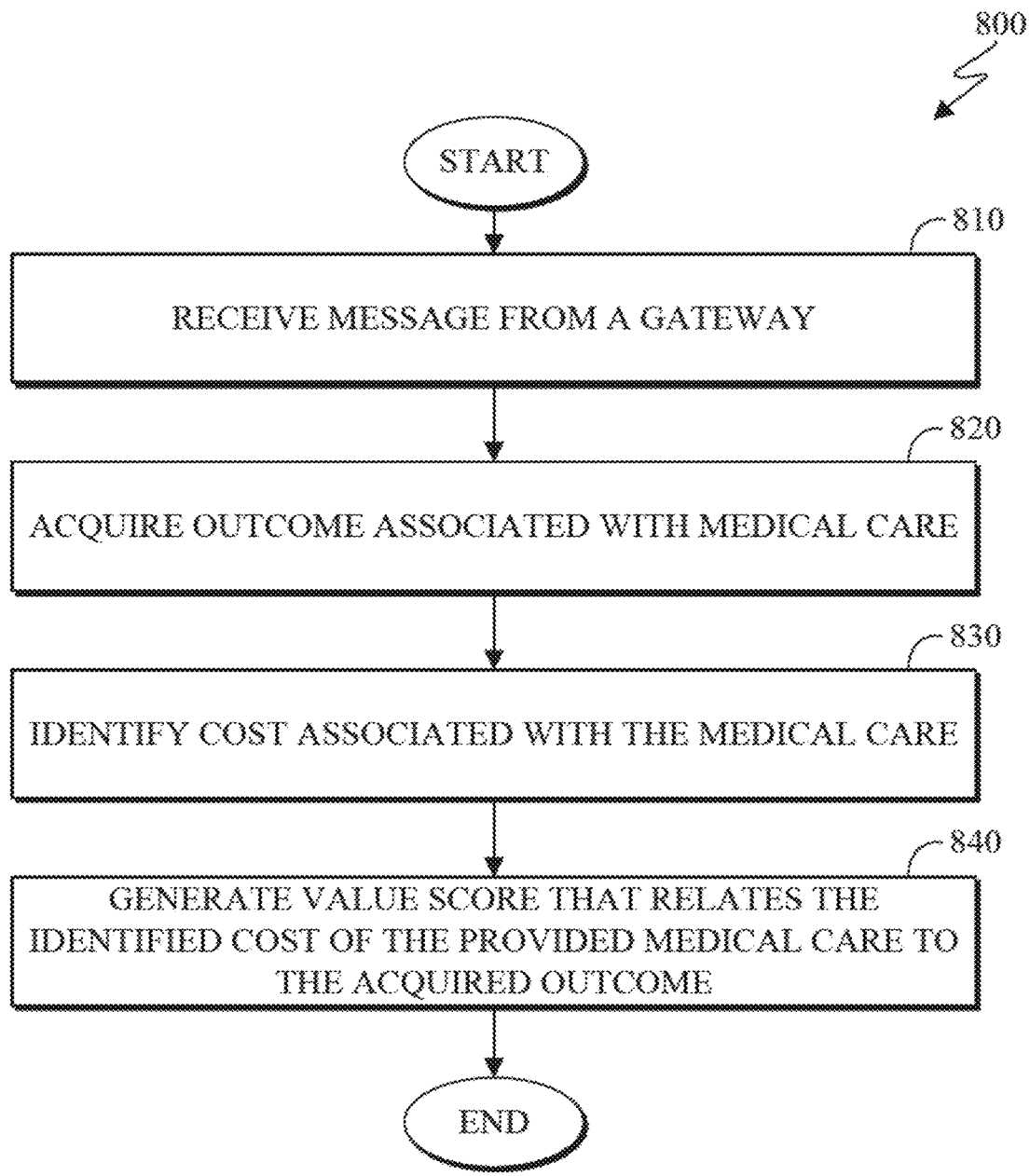
FIG. 8 illustrates a method for deriving a value associated with medical-care in accordance with embodiments of the present disclosure.

FIG. 8 illustrates a method for deriving a value associated with medical-care in accordance with embodiments of the present disclosure. While process 800 depicts a series of sequential steps, unless explicitly stated, no inference should be drawn from that sequence regarding specific order of performance, performance of steps or portions thereof serially rather than concurrently or in an overlapping manner or performing of the steps depicted exclusively without the occurrence of intervening or intermediate steps. For ease of explanation, the method of determining an operation to perform based on contextual information is described with respect to the server 200 of FIG. 2, the electronic device 300 of FIG. 3, the value server 630 of FIG. 6, and the server 730 of FIG. 7; however the process 800 can be used with any suitable system.

At step 810 the server 730 receives a message from a gateway. The gateway that sent the message sent the message in response to reciting a ping from a beacon. The received message includes an identification parameter that identifies the gateway that sent the message. The message also includes a beacon identifier. The beacon identifier identifies the beacon that transmitted the ping to the gateway. The ping that was transmitted from the beacon to the gateway includes the beacon identifier. The message also includes a derived signal strength parameter. The signal strength parameter is derived by the gateway and indicates a proximity the gateway is from the beacon when the ping form the beano is received by the gateway.

At step 820 the server 730 acquires an outcome associated with medical-care. The outcome can be associated with medical-care that is provided by a medical provider to a patient. The outcome can be derived based on received geospatial data of a location of the patient after the medical-care is provided to the patient by the medical provider. In certain embodiments, the outcome can be associated with a numerical value that is derived from patient surveys indicating opinions of the patient regarding the medical-care received. The outcome can be based on empirical data including results of the medical-care. In certain embodiments, the outcome can be based on re-admittance to a medical facility within a predetermined number of days following the medical-care. Furthermore, the outcome can be based on mortality within a predefined quantity of days following the medical-care provided by the medical provider.

In certain embodiments, the server 730 generates a survey that encompasses the medical-care received by the patient. The server 730 can then transmit the generated survey to the patient during or following the medical-care. Thereafter the server 730 can receive the survey willed out by the patient. In certain embodiments, the survey can input portions of the survey as filled out by the patient as the acquired outcome associated with the received medical-care.

At step 830 the server 730 identifies cost associated with the medical-care. The identified cost is based on the received message from the gateway. To identify costs associated with the medical-care the server 730 can identify locations within a medical facility that the patient is located based on the received message from the gateway. The server 730 can also deriving a first set of time durations for each of the location that the patient is located within the medical facility for the medical-care. Each of the locations can include a particular rate associated therewith. A second set of time durations can be derived. The second set of time durations include the time that the medical provider is providing the medical-care to the patient. The second set of time durations can be based on an cation from the one or more messages that the beacon of the medical provider and the beacon of the patient are in proximity to each other. Thereafter, the cost can be determined based on the first set of time durations and the second set of time durations. In certain embodiments, the determined cost can also include identifying a second set of costs associated with the medical-care provided to the patient, such as supplies, testing, procedures, equipment use, and the like. In certain embodiments, the identified costs include comparing billed invoices and collected money for the medical-care provided by the medical provider.

At step 840 the server 730 generates a value score. The value score relates the identified cost of the provided medical-care to the acquired outcome. In certain embodiments, the server 730 generates an array of value scores. The array of value scores can be based in part on the plurality of outcomes, the plurality of costs, and the plurality of medical conditions. The server 730 can identify a particular medical intervention that can be provided by a subsequent patient based on the similar demographics. The identified medical intervention is based on a value score that indicates a high outcome with a low cost.

Although the figures illustrate different examples of user equipment, various changes may be made to the figures. For example, the user equipment can include any number of each component in any suitable arrangement. In general, the figures do not limit the scope of this disclosure to any particular configuration(s). Moreover, while figures illustrate operational environments in which various user equipment features disclosed in this patent document can be used, these features can be used in any other suitable system.

None of the description in this application should be read as implying that any particular element, step, or function is an essential element that must be included in the claim scope. The scope of patented subject matter is defined only by the claims. Moreover, none of the claims is intended to invoke 35 U.S.C. § 112(f) unless the exact words "means for" are followed by a participle. Use of any other term, including without limitation "mechanism," "module," "device," "unit," "engine," "component," "element," "member," "apparatus," "machine," "system," "processor," or "controller," within a claim is understood by the applicants to refer to structures known to those skilled in the relevant art and is not intended to invoke 35 U.S.C. § 112(f).

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. A system for value derivation, the system comprises:
one or more gateways located in predefined locations within a medical facility, and each of the one or more gateways include a transceiver, a first processor, and an identification parameter, the identification parameter is unique to each of the one or more gateways and corresponds to each of the predefined locations; and
a computing device including a communication interface and a second processor,
wherein the transceiver is operably connected to the first processor and configured to:
receive a ping from a beacon, the ping includes a beacon identifier that is unique to the beacon, wherein the beacon is associated with a medical provider or a patient, and
transmit a message to the computing device in response to receiving the ping,
wherein the first processor is configured to:
derive a signal strength parameter associated with the received ping, the signal strength parameter indicates strength of the received ping, generate the message that includes the beacon identifier, the identification parameter associated with one gateway that received the ping, and the signal strength parameter,
in response to receiving the ping, determine whether a previously received ping was received from the beacon within a threshold period,
identify whether the signal strength parameter associated with the received ping from the beacon matches a previously derived signal strength parameter associated with the previously received ping from the beacon, and
when the signal strength parameter associated with the received ping matches the previously derived signal strength parameter associated with the previously received ping from the same beacon, and the received ping and the previously received ping from the beacon were received within the threshold period, prevent the transceiver from transmitting the message to the computing device,
wherein the communication interface is operably connected to the second processor and configured to receive the message, and
wherein the second processor is configured to:
acquire an outcome associated with medical-care that is provided by the medical provider to the patient,
identify a cost associated with the medical-care provided by the medical provider to the patient based on the received message, and
generate a value score that relates the identified cost of the medical-care provided by the medical provider to the patient, to the acquired outcome.

2. The system of claim 1, wherein:
at least one gateway of the one or more gateways receives the ping from the beacon,
the communication interface is further configured to receive one or more messages from each of the at least one gateway that received the ping from the beacon, and
the second processor is further configured to:
compare the signal strength parameter from each of the received one or more messages to identify a strongest signal strength parameter, and
in response to identifying the strongest signal strength parameter, assign a location to the beacon that corresponds to the predefined location of the one gateway that transmitted the message that included the identified strongest signal strength parameter, based on the identification parameter of the one gateway.

3. The system of claim 1, wherein to identify the cost the second processor is further configured to:
track the beacon as the beacon moves throughout the medical facility;
derive a time duration that the beacon is located in each location as the beacon moves throughout the medical facility; and
determine a cost associated with the beacon at the each of the locations within the medical facility, the cost is based on a rate associated with each of the locations and the time duration that the beacon is located in each of the locations.

4. The system of claim 1, wherein the beacon includes a first beacon and a second beacon, the first beacon is associated with the patient, and the second beacon is associated with the medical provider,
wherein to identify the cost associated with the medical-care, the second processor is further configured to:
derive a first set of time durations for each location that a first beacon is within the medical facility for the medical-care, wherein each of the locations includes a particular rate associated therewith;
derive a second set of time durations that a second beacon is providing the medical-care to the patient; and
determine the cost based on the first set of time durations that the patient is located in each of the locations within the medical facility and the second set of time durations.

5. The system of claim 1, wherein the outcome associated with the medical-care is based on at least one of:
a numerical value that is derived from patient surveys indicating opinions of the patient regarding the medical-care received;
empirical data including results of the medical-care;
re-admittance to a medical facility within a predetermined number of days following the medical-care; and
mortality within a predefined quantity of days following the medical-care provided by the medical provider.

6. The system of claim 1, wherein to acquire the outcome associated with the medical-care, the second processor is further configured to receive geospatial data of a location of the patient based on the beacon that is associated with the patient, after the medical-care is provided to the patient by the medical provider.

7. The system of claim 1, wherein to acquire the outcome associated with the medical-care:
the second processor is further configured to:
generate a survey that encompasses the medical-care received by the patient, and
after receiving the survey completed by the patient, input a portion of the received survey as the acquired outcome, and
the communication interface further configured to:
transmit the generated survey to the patient, and
receive the survey from the patient, wherein the received survey is completed by the patient.

8. A method for value derivation, the method comprises:
receiving a message from a gateway, wherein
the message includes:
an identification parameter associated with the gateway that received a ping from a beacon,
a beacon identifier of the beacon that transmitted the ping to the gateway, the ping included the beacon identifier, and
a derived signal strength parameter, the derived signal strength parameter indicates a proximity of the beacon to the gateway when the beacon transmitted the ping, and
in response to receiving the ping, determining whether a previously received ping was received from the beacon within a threshold period,
identifying whether the signal strength parameter associated with the received ping from the beacon matches a previously derived signal strength parameter associated with the previously received ping from the beacon, and
when the signal strength parameter associated with the received ping matches the previously derived signal strength parameter associated with the previously received ping from the same beacon, and the received ping and the previously received ping from the beacon were received within the threshold period, preventing the transceiver from transmitting the message to the computing device;

acquiring an outcome associated with medical-care that is provided by a medical provider to a patient;
identifying a cost associated with the medical-care provided by the medical provider to the patient based in part on the received message from the gateway; and
generating a value score that relates the identified cost of providing the medical-care by the medical provider to the patient, to the acquired outcome.

9. The method of claim 8, wherein the gateway includes one or more gateways and the message includes one or more message from the one or more gateways, the beacon includes a first beacon that is associated with the patient and a second beacon that is associated with the medical provider, and
wherein to identify the cost associated with the medical-care, the method comprises:
identifying locations within a medical facility that the patient is located based on the received message from the gateway;
deriving a first set of time durations for each of the location that the patient is located within the medical facility for the medical-care, wherein the locations includes a particular rate associated therewith,
deriving a second set of time durations that the medical provider is providing the medical-care to the patient, based on an indication from the one or more messages that the beacon of the medical provider and the beacon of the patient are in proximity to each other, and
determining the cost based on the first set of time durations and the second set of time durations.

10. The method of claim 9, wherein determining the cost further comprises identifying a second set of costs associated with the medical-care provided to the patient.

11. The method of claim 8, wherein to identify the cost associated with the medical-care, the method further comprises comparing billed invoices and collected money for the medical-care provided by the medical provider.

12. The method of claim 8, wherein the outcome associated with the medical-care is based on at least one of:
a numerical value that is derived from patient surveys indicating opinions of the patient regarding the medical-care received;
empirical data including results of the medical-care;
re-admittance to a medical facility within a predetermined number of days following the medical-care; and
mortality within a predefined quantity of days following the medical-care provided by the medical provider.

13. The method of claim 8, wherein to acquire the outcome associated with the medical-care comprises, receiving geospatial data of a location of the patient after the medical-care is provided to the patient by the medical provider.

14. The method of claim 8, wherein to acquire the outcome associated with the medical-care comprises:
generating a survey that encompasses the medical-care received by the patient;
transmitting the generated survey to the patient;
receiving the survey from the patient, wherein the received survey is completed by the patient; and
after receiving the survey from the patient, inputting a portion of the received survey as the acquired outcome.

15. The method of claim 8, wherein the acquired outcome is one of a plurality of outcomes, the identified cost is one of a plurality of costs, the patient is one of a plurality of patients, the medical provider is one of a plurality of medical providers, and the medical-care is associated with one of a plurality of medical conditions, and
wherein the method further comprises:
generating an array of value scores based in part on the plurality of outcomes, the plurality of costs, and the plurality of medical conditions, and
identifying a particular medical-care to provide to a new patient that is associated with a first medical condition of the plurality of medical conditions, the particular medical-care is based on one value score of the array of value scores that is associated with the first medical condition and the one value score indicates a highest outcome with a lowest cost.

16. A non-transitory computer readable medium embodying a computer program, the computer program comprising computer readable program code that when executed by a processor of an electronic device causes the processor to:
receive a message from a gateway, wherein
the gateway includes a transceiver, a first processor, and an identification parameter,
the message includes:
an identification parameter associated with the gateway that received a ping from a beacon,
a beacon identifier of the beacon that transmitted the ping to the gateway, the ping included the beacon identifier, and
a derived signal strength parameter, the derived signal strength parameter indicates a proximity of the beacon to the gateway when the beacon transmitted the ping, and
in response to receiving the ping, determine whether a previously received ping was received from the beacon within a threshold period,
identify whether the signal strength parameter associated with the received ping from the beacon matches a previously derived signal strength parameter associated with the previously received ping from the beacon, and
when the signal strength parameter associated with the received ping matches the previously derived signal strength parameter associated with the previously received ping from the same beacon, and the received ping and the previously received ping from the beacon were received within the threshold period, prevent the transceiver from transmitting the message to the computing device;
acquire an outcome associated with medical-care that is provided by a medical provider to a patient;
identify a cost associated with the medical-care provided by the medical provider to the patient based in part on the received message from the gateway; and
generate a value score that relates the identified cost of providing the medical-care by the medical provider to the patient, to the acquired outcome.

17. The non-transitory computer readable medium of claim 16, wherein the gateway includes one or more gateways and the message includes one or more messages from the one or more gateways, the beacon includes a first beacon that is associated with the patient and a second beacon that is associated with the medical provider, and
wherein to identify the cost associated with the medical-care, the non-transitory computer readable medium further comprises program code that, when executed at the processor, causes the processor to:
identify locations within a medical facility that the patient is located based on the received message from the gateway;

derive a first set of time durations for each of the location that the patient is located within the medical facility for the medical-care, wherein the locations includes a particular rate associated therewith, derive a second set of time durations that the medical provider is providing the medical-care to the patient, based on an indication from the one or more messages that the beacon of the medical provider and the beacon of the patient are in proximity to each other, and determine the cost based on the first set of time durations and the second set of time durations.

18. The non-transitory computer readable medium of claim 16, wherein to acquire the outcome associated with the medical-care, the non-transitory computer readable medium further comprises program code that, when executed at the processor, causes the processor to receive geospatial data of a location of the patient after the medical-care is provided to the patient by the medical provider.

19. The non-transitory computer readable medium of claim 16, wherein to acquire the outcome associated with the medical-care, the non-transitory computer readable medium further comprises program code that, when executed at the processor, causes the processor to:

generate a survey that encompasses the medical-care received by the patient;

transmit the generated survey to the patient;

receive the survey from the patient, wherein the received survey is completed by the patient; and after receiving the survey from the patient, input a portion of the received survey as the acquired outcome.

\* \* \* \* \*